(12) United States Patent
Mahato et al.

(10) Patent No.: US 6,696,038 B1
(45) Date of Patent: Feb. 24, 2004

(54) CATIONIC LIPOPOLYMER AS BIOCOMPATIBLE GENE DELIVERY AGENT

(75) Inventors: Ram I. Mahato, Murray, UT (US); Sang-Oh Han, Salt Lake City, UT (US); Darin Y. Furgeson, Salt Lake City, UT (US)

(73) Assignee: Expression Genetics, Inc., Sandy, UT (US)

( * ) Notice: Subject to any disclaimer, the term of this patent is extended or adjusted under 35 U.S.C. 154(b) by 0 days.

(21) Appl. No.: 09/662,511

(22) Filed: Sep. 14, 2000

(51) Int. Cl.$^7$ ............................................... A61K 51/00
(52) U.S. Cl. ..................... 424/1.45; 530/402; 424/450; 525/7; 554/35; 564/123; 564/270
(58) Field of Search ............................ 435/458, 252.3, 435/325; 514/44, 1, 2, 8, 12, 23, 53, 54; 424/450, 1.45; 525/54.5, 540, 7; 554/35, 51, 63; 530/402; 564/1, 123, 270; 585/17

(56) References Cited

U.S. PATENT DOCUMENTS

| | | | |
|---|---|---|---|
| 4,121,982 A | * 10/1978 | Moriarty et al. | .............. 204/43 |
| 5,283,185 A | 2/1994 | Epand et al. | |
| 5,393,335 A | 2/1995 | Puckett et al. | |
| 5,476,989 A | * 12/1995 | Mimori et al. | ................ 588/20 |
| 5,753,262 A | 5/1998 | Wyse et al. | |
| 5,945,400 A | 8/1999 | Scherman et al. | |
| 5,955,415 A | * 9/1999 | Gutierrez et al. | ........... 510/312 |
| 6,177,274 B1 | * 1/2001 | Park et al. | .................. 435/455 |

OTHER PUBLICATIONS

W. French Anderson, Human gene therapy, Nature, vol. 392, Apr. 30, 1998, pp. 25–30.*

Inder M. Verma et al., Gene therapy—promises, problems and prospects, Nature, vol. 389, Sep. 18, 1997, pp. 239–242.*

Nicholas Miller et al., Targeted vectors for gene therapy, (FASEB J. 9: 190–194, 1995).*

Ronald G. Crystal, Transfer of Genes of Humans: Early Lessons and Obstacles to Success, Science 1995, vol. 270, pp. 404–410.*

Mahendra P. Deonarain, Ligand–targeted receptor–mediated vectors for gene delivery, (Exp. Opin. Ther. Patents 8(1):53–69, 1998).*

M Ogris et al., PEGylated DNA/transferrin–PEI complexes: reduced interaction with blood components, extended circulation in blood and potential for systemic gene delivery, Gene Therapy 1996 6, pp. 595–605.*

W.T. Godbey et al., Poly(ethylenimine) and its role in gene delivery, Journal of Controlled Release 60 (1999) pp. 149–160.*

Felgner PL, et al., Lipofection: A Highly Efficient, Lipid–Mediated DNA Transfection Procedure, *Proc Natl Acad Sci USA* USA 84: 7413–7417 (1987).

Gao, X. and Huang L., A Novel Cationic Liposome Reagent for Efficient Transfection of Mammalian Cells, *Biochem. Biophys. Res. Commun.* 179: 280–285 (1991).

Nabel, et al., Gene Transfer in vivo with DNA–Liposome Complexes, *Human Gene Therapy* 3:649–656, (1992b).

T. Mosmann, Rapid Colorimetric Assay for Cellular Growth and Survival: Application to Proliferation and Cytotoxicity Assays, 65 *J. Immunol. Methods* 55–63 (1983).

* cited by examiner

*Primary Examiner*—Dave T. Nguyen
*Assistant Examiner*—Richard Schnizer
(74) *Attorney, Agent, or Firm*—Thorpe North & Western, LLP

(57) ABSTRACT

A biodegradable, novel cationic lipopolymer comprising a branched polyethylenimine(PEI), a cholesterol derived lipid anchor, and a biodegradable linker which covalently links the branched PEI and cholesterol derived lipid anchor. One example of such a novel lipolymer is poly{(ethylene imine)-co-[N-2-aminoehtyl)ethylene imine]-co-[N-(N-cholesteryloxycabonyl-(2-aminoethyl))ethylene imine]} ("PEACE"). The cationic lipopolymers in the present invention can be used in drug delivery and are especially useful for delivery of a nucleic acid or any anionic bioactive agent to various organs and tissues after local or systemic administration. Methods of preparing and using the cationic lipopolymer gene carriers of the present invention to efficiently transfect cells, both in vitro and in vivo, are disclosed.

12 Claims, 13 Drawing Sheets

Lane 1: 100 bp ladder, lane 2 & 4 : PEACE:DOPE (1/1)/pmIL-12 (1/1, +/-) β-actin, lane 3 & 5 : PEACE:DOPE (1/1)/pmIL-12 (1/1, +/-) mIL-12 p35, lane 6 & 8: PEACE:DOPE (1/1)/pmIL-12 (5/1, +/-) β-actin, lane 7 & 9 : PEACE:DOPE (1/1)/pmIL-12 (5/1, +/-) mIL-12 p35, lane 10 & 12 : PEACE:DOPE (2/1)/pmIL-12 (3/1, +/-) β-actin, lane 11 & 13: PEACE:DOPE (2/1)/pmIL-12 (3/1, +/-) mIL-12 p35, lane 14: 100 bp ladder.

CATIONIC LIPOPOLYMER AS BIOCOMPATIBLE GENE DELIVERY AGENT

FIELD OF THE INVENTION

This invention relates to delivery of a bioactive agent. More particularly, the invention relates to a composition and method for delivering bioactive agents, such as DNA, RNA, oligonucleotides, proteins, peptides, and drugs, by facilitating their transmembrane transport or by enhancing their adhesion to biological surfaces. It relates particularly to a novel cationic lipopolymer comprising a branched polyethylenimine (PEI), a cholesterol derived lipid anchor, and a biodegradable linker which covalently links the branched PEI and cholesterol derived lipid anchor. One example of such a novel lipolymer is poly {(ethylene imine)-co-[N-2-aminoethyl)ethylene imine]-co-[N-(N-cholesteryloxycabonyl-(2-aminoethyl))ethylene imine]} (hereafter referred to as "PEACE"). The cationic lipopolymers of the present invention can be used in drug delivery and are especially useful for delivery of a nucleic acid or any anionic bioactive agent.

BACKGROUND OF THE INVENTION

Gene therapy is generally considered as a promising approach not only for the treatment of diseases with genetic defects but also in the development of strategies for treatment and prevention of chronic diseases such as cancer, cardiovascular disease and rheumatoid arthritis. However, nucleic acids as well as other polyanionic substances are rapidly degraded by nucleases and exhibit poor cellular uptake when delivered in aqueous solutions. Since early efforts to identify methods for delivery of nucleic acids in tissue culture cells in the mid 1950's, steady progress has been made towards improving delivery of functional DNA, RNA, and antisense oligonucleotides in vitro and in vivo.

The gene carriers used so far include viral systems (retroviruses, adenoviruses, adeno-associated viruses, or herpes simplex viruses) or nonviral systems (liposomes, polymers, peptides, calcium phosphate precipitation and electroporation). Viral vectors have been shown to have high transfection efficiency when compared to non-viral vectors, but due to several drawbacks, such as targeting only dividing cells, random DNA insertion, their low capacity for carrying large sized therapeutic genes, risk of replication, and possible host immune reaction, their use in vivo is severely limited.

Compared to viral vectors, nonviral vectors are easy to make and less likely to produce immune reactions, and there is no replication reaction required. There has been increasing attention focused on the development of safe and efficient nonviral gene transfer vectors, which are either polycationic polymers or cationic lipids. Polycationic polymers such as poly-L-lysine, poly-L-omithine and polyethyleneimine (PEI), that interact with DNA to form polyionic complexes, have been introduced for use in gene delivery. Various cationic lipids have also been shown to form lipoplexes with DNA and induce efficient transfection of various eukaryotic cells. Among such kinds of synthetic vectors, cationic lipids are widely used because it is possible to design and synthesize numerous derivatives that are outstanding in the aspects of transfection efficiency, biodegradability and low toxicity. Many different cationic lipids are commercially available and several lipids have already been used in the clinical setting. Among them, cationic cholesterol derivatives are known to be very useful because of their high transfection efficiency in vitro. Although the mechanism of this transfection activity is not yet clear, it probably involves binding of the DNA/lipid complex with the cell surface via excess positive charges on the complex. Cell surface bound complexes are probably internalized and the DNA released into the cytoplasm of the cell from an endocytic compartment.

However, it is not feasible to directly extend in vitro transfection technology to in vivo applications. Relative to in vivo use, the biggest drawback of the diether lipids, such as N-[1-(2,3-dioleyloxy)propyl]-N,N,N-trimethyl ammonium chloride (DOTMA) or Lipofectin is that they are not natural metabolites of the body, and are thus not biodegradable and they are toxic to cells. In addition, it has been reported that cationic lipid transfection is inhibited by factors present in serum and thus it is an ineffective means for the introduction of genetic material into cells in vivo.

An ideal transfection reagent should exhibit a high level of transfection activity without needing any mechanical or physical manipulation of the cells or tissues. The reagent should be non-toxic, or minimally toxic, at the effective dose. In order to avoid any long-term adverse side-effects on the treated cells, it should also be biodegradable. When gene carriers are used for delivery of nucleic acids in vivo, it is essential that the gene carriers themselves be nontoxic and that they degrade into non-toxic products. To minimize the toxicity of the intact gene carrier and its degradation products, the design of gene carriers needs to be based on naturally occurring metabolites. U.S. Pat. No. 5,283,185, to Epand et al. (hereafter the '185 patent), discloses a method for facilitating the transfer of nucleic acids into cells comprising preparing a mixed lipid dispersion of a cationic lipid. 3β[N-(N',N"-dimethylaminoethane)-carbamoyl]cholesterol (DC-cholesterol) with a co-lipid in a suitable carrier solvent. The method disclosed in the '185 patent involves using a halogenated solvent in preparing a liposome suspension. For pharmaceutical applications, residues of halogenated solvents cannot be practically removed from a preparation after having been introduced. U.S. Pat. No. 5,753,262, (hereafter the '262 patent) discloses using the acid salt of the lipid 3β[N-(N',N"-dimethylaminoethane)-carbamoyl]cholesterol (DC-cholesterol) and a helper lipid such as dioleoyl phosphatidylethanolamine (DOPE) or dioleoylphosphatidylcholine (DOPC) to produce effective transfection in vitro. In addition, these cationic lipids have been proven less efficient in gene transfer in vivo.

Because of their sub-cellular size, nanoparticles are hypothesized to enhance interfacial cellular uptake, thus achieving in a true sense a "local pharmacological drug effect." It is also hypothesized that there would be enhanced cellular uptake of drugs contained in nanoparticles (due to endocytosis) compared to the corresponding free drugs. Nanoparticles have been investigated as drug carrier systems for tumor localization of therapeutic agents in cancer therapy, for intracellular targeting (antiviral or antibacterial agents), for targeting to the reticuloendothelial system (parasitic infections), as an immunological adjuvant (by oral and subcutaneous routes), for ocular delivery with sustained drug action, and for prolonged systemic drug therapy.

In view of the foregoing, it will be appreciated that providing a gene carrier that is non-toxic, biodegradable, and capable of forming nanoparticles, liposomes, or micelles for gene therapy and drug delivery, is desired. The novel gene carrier of the present invention comprises a novel cationic lipopolymer comprising a branched polyethylenimine(PEI), a cholesterol derived lipid anchor, and a biodegradable linker which covalently links the branched PEI and cholesterol derived lipid anchor. The lipolymer of the present invention is useful for preparing a cationic liposome, or a cationic micelle for drug delivery, especially for delivery of nucleic acids, other anionic bioactive molecules or both and is readily susceptible to metabolic degradation after incorporation into the cell.

BRIEF SUMMARY OF THE INVENTION

The present invention provides a biodegradable cationic lipopolymer, having reduced in vivo and in vitro toxicity, for delivery of drugs or other bioactive agents to an individual in need thereof.

The present invention also provides a cationic lipopolymer for delivery of nucleic acids which carries out both stable and transient transfection of polynucleotides such as DNA and RNA into cells more effectively.

The biodegradable, non-toxic cationic lipopolymer of the present invention comprises a branched polyethylenimine (PEI), a cholesterol derived lipid anchor, and a biodegradable linker which covalently links the branched PEI and cholesterol derived lipid anchor. Preferably, the average molecular weight of the branched PEI is within a range of 600 to 25,000 Daltons. The branched PEI is preferably conjugated to the cholesterol derivative by an ester bond. The molar ratio of the branched PEI to the conjugated cholesterol derivative is preferably within a range of 1:1 to 1:20.

By adjusting the molecular weight of the branched PEI and the molar ratio of the branched PEI to conjugated cholesterol derivative, the resultant lipolymer can be either water soluble or water insoluble. For example, to obtain a water soluble lipopolymer, the average molecular weight of the branched PEI is preferably within a range of 1800 to 25,000, and the molar ratio of the branched PEI to the conjugated cholesterol derivative is preferably within a range of 1:1 to 1:5. To obtain a water insoluble lipopolymer, the average molecular weight of the branched PEI is preferably within a range of 600 to 1800, and the molar ratio of the branched PEI to the conjugated cholesterol derivative is preferably within a range of 1:1 to 1:2. Although a cholesterol derived lipid anchor is preferred in the present invention, other lipophilic moieties may also be used, such as $C_{12}$ to $C_{18}$ saturated or unsaturated fatty acids.

The biodegradable lipopolymers can be synthesized by relatively simple and inexpensive methods. These cationic lipopolymers invention can spontaneously form discrete nanometer-sized particles with a nucleic acid, which can promote more efficient gene transfection into mammalian cell lines than can be achieved conventionally with Lipofectin and polyethyleneimine. The lipopolymer the present invention is readily susceptible to metabolic degradation after incorporation into animal cells. Moreover, the water soluble cationic lipopolymer can form an aqueous micellar solution which is particularly useful for systemic delivery of various bioactive agents such as DNA, proteins, hydrophobic or hydrophilic drugs. The water insoluble lipopolymer can form cationic liposomes with a helper, which is particularly useful for local drug delivery. Therefore, the biocompatible and biodegradable cationic lipopolymer of this invention provides an improved gene carrier for use as a general reagent for transfection of mammalian cells, and for the in vivo application of gene therapy.

The present invention further provides transfection formulations, comprising a novel cationic lipopolymer, complexed with a selected nucleic acid in the proper charge ratio(positve charge of the lipopolymer/negative charge of the nucleic acid) that is optimally effective for both in vivo and in vitro transfection. Particularly, for systemic delivery, the charge ratio (+/−) is preferably 5/1 to 1/1; for local delivery, the charge ratio (+/−) is preferably 3/1 to 0.5/1.

This invention also provides for a method of transfecting, both in vivo and in vitro, a nucleic acid into a mammalian cell. The method comprises contacting the cell with a cationic lipopolymer or liposome:nucleic acid complexes as described above. In one embodiment, the method uses systemic administration of the cationic lipopolymer or liposome:nucleic acid complexes into a warm blooded animal. In a preferred embodiment, the method of transfecting uses intravenous administration of the cationic lipopolymer or liposome:nucleic acid complexes into a warm blooded animal. In a particularly preferred embodiment, the method comprises intravenous injection of water soluble PEACE/pDNA and PEACE:DOPE liposomes/pDNA complexes into a warm blooded animal.

DETAILED DESCRIPTION

Figure 1:
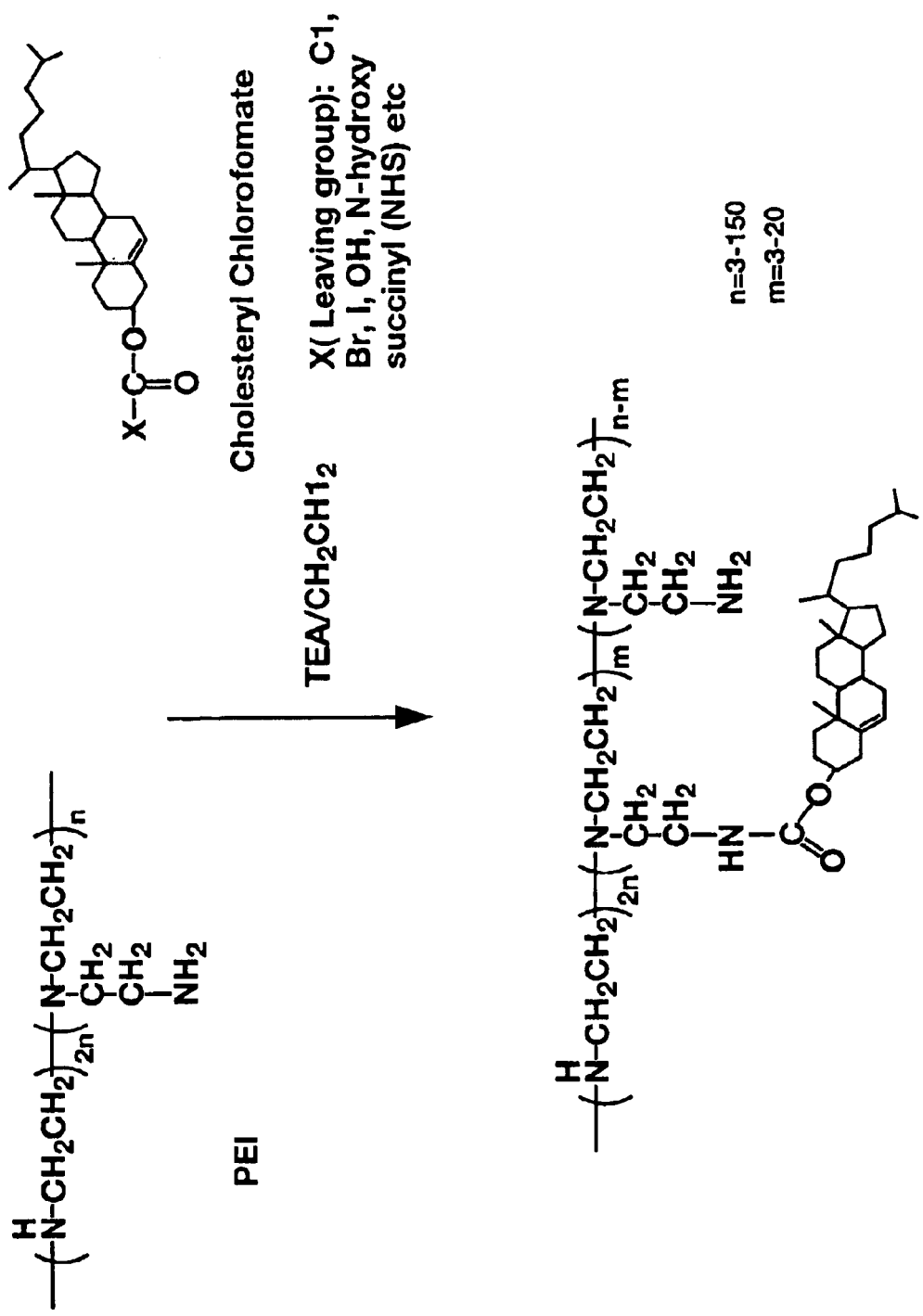
FIG. 1 illustrates a synthetic scheme for poly{(ethylene imine)-co-[N-2-aminoehtyl)ethylene imine]-co-[N-(N-cholesteryloxycabonyl-(2-aminoethyl))ethylene imine]} ("PEACE").

Before the present composition and method for delivery of a bioactive agent are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof It must be noted that, as used in this specification and the appended claims, the singular forms "a," "an," and "the" include plural referents unless the context clearly dictates otherwise. Thus, for example, reference to a polymer containing "a sugar" includes reference to two or more of such sugars, reference to "a ligand" includes reference to one or more of such ligands, and reference to "a drug" includes reference to two or more of such drugs.

In describing and claiming the present invention, the following terminology will be used in accordance with the definitions set out below.

"Transfecting" or "transfection" shall mean transport of nucleic acids from the environment external to a cell to the internal cellular environment, with particular reference to the cytoplasm and/or cell nucleus. Without being bound by any particular theory, it is understood that nucleic acids may be delivered to cells either in forms or after being encapsulated within or adhering to one or more cationic lipid/nucleic acid complexes or entrained therewith. Particular transfecting instances deliver a nucleic acid to a cell nucleus. Nucleic acids include both DNA and RNA as well as synthetic congeners thereof. Such nucleic acids include missense, antisense, nonsense, as well as protein producing nucleotides, on and off and rate regulatory nucleotides that control protein and peptide, and nucleic acid production. In particular, but nonlimiting, they can be genomic DNA, cDNA, mRNA, tRNA, rRNA, hybrid sequences or synthetic or semi-synthetic sequences and of natural or artificial origin. In addition, the nucleic acid can be variable in size, ranging from oligonucleotides to chromosomes. These nucleic acids may be of human, animal, vegetable, bacterial, viral, and the like, origin. They may be obtained by any technique known to a person skilled in the art.

As used herein, the term "bioactive agent" or "drug" or any other similar term means any chemical or biological material or compound suitable for administration by the methods previously known in the art and/or by the methods taught in the present invention that induce a desired biological or pharmacological effect, which may include but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating a disease from the organism. The effect may be local, such as providing for a local anaesthetic effect, or it may be systemic.

This invention is not drawn to novel drugs or to new classes of bioactive agents. Rather it is limited to the compositions and methods of delivery of genes or other bioactive agents that exist in the state of the art or that may later be established as active agents and that are suitable for delivery by the present invention. Such substances include broad classes of compounds normally delivered into the body. In general, this includes but not limited to: nucleic acids, such as DNA, RNA, and oligonucleotides., antiinfectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium, calcium channel blockers, beta-blockers, alpha-blockers, and antiarrhythmics; antihypertensives; diuretics and antidiuretics; vasodilators including general, coronary, peripheral and cerebral; central nervous system stimulants; vasoconstrictors; cough and cold preparations, including decongestants; hormones such as estradiol and other steroids including corticosteroids; hypnotics; immunosuppressives; muscle relaxants; parasympatholytics; psychostimulants; sedatives; and tranquilizers. By the method of the present invention, drugs in all forms, e.g. ionized, nonionized, free base, acid addition salt, and the like may be delivered, as can drugs of either high or low molecular weight.

As used herein, "effective amount" means an amount of a nucleic acid or a bioactive agent that is nontoxic but sufficient to provide the desired local or systemic effect and performance at a reasonable risk/benefit ratio that would attend any medical treatment.

As used herein, "peptide", means peptides of any length and includes proteins. The terms "polypeptide" and "oligopeptide" are used herein without any particular intended size limitation, unless a particular size is otherwise stated. Typical of peptides that can be utilized are those selected from the group consisting of oxytocin, vasopressin, adrenocorticotrophic hormone, epidermal growth factor, prolactin, luliberin or luteinising hormone releasing hormone, growth hormone, growth hormone releasing factor, insulin, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines. The only limitation to the peptide or protein drug which may be utilized is one of functionality.

As used herein, a "derivative" of a carbohydrate includes, for example, an acid form of a sugar, e.g. glucuronic acid; an amine of a sugar, e.g. galactosamine; a phosphate of a sugar, e.g. mannose-6-phosphate; and the like.

As used herein, a "liposome" means a microscopic vesicle composed of uni-or multilamliar bilayer or bilayers surrounding aqueous compartments.

As used herein, "administering", and similar terms means delivering the composition to the individual being treated such that the composition is capable of being circulated systemically where the composition binds to a target cell and is taken up by endocytosis. Thus, the composition is preferably administered to the individual systemically, typically by subcutaneous, intramuscular, intravenous, or intraperitoneal administration. Injectables for such use can be prepared in conventional forms, either as a liquid solution or suspension, or in a solid form that is suitable for preparation as a solution or suspension in a liquid prior to injection, or as an emulsion. Suitable excipients include, for example, water, saline, dextrose, glycerol, ethanol, and the like; and if desired, minor amounts of auxiliary substances such as wetting or emulsifying agents, buffers, and the like can be added.

Fundamental to the success of gene therapy is the development of gene delivery vehicles that are safe and efficacious after systemic administration. Many of the cationic lipids used in the early clinical trials, such as N[1-(2,3-dioleyloxy)propyl]-N,N, N-trimethylammonium chloride (DOTMA) and 3-β(N,N"-dimethylaminoethane cabamoyl cholesterol) (DC-Chol) although exhibiting efficient gene transfer in vitro, have been proven less efficient in gene transfer in animals. See. Felgner PL et.al Lipofection: A highly efficient, lipid-mediated DNA transfection procedure. *Proc Natl Acad Sci USA* 84: 7413–7417 (1987); and Gao, X. and Huang L. (1991) A novel cationic liposome reagent for efficient transfection of mammalian cells. *Biochem. Biophys. Res. Commun.* 179: 280–285.

The general structure of a cationic lipid has three parts: (i) a hydrophobic lipid anchor, which helps in forming liposomes (or micellar structures) and interacts with cell membranes; (ii) a linker group; and (iii) a positively charged head-group, which interacts with the plasmid, leading to its condensation. Many compounds bearing either a single tertiary or quaternary ammonium head-group or which contain protonatable polyamines linked to dialkyl lipid or cholesterol anchors have been used for transfection into various cell types. The orientation of the polyamine head-group in relation to the lipid anchor has been shown to greatly influence the transfection efficiency. Conjugation of spermine or spermidine head-groups to the cholesterol lipid anchor via a carbamate linkage through a secondary amine to generate T-shape cationic lipids has been shown to be very effective in gene transfer to the lung. In contrast, the generation of a linear polyamine lipid by conjugating spermine or spermidine to cholesterol or a dialkyl lipid anchor was much less effective in gene transfer.

A cationic lipid which contains three protonatable amines in its head-group has been shown to be more active than DC-Cholesterol, which contains only one protonatable amine. In addition to the number of protonatable amines, the choice of the linkar group bridging the hydrophobic lipid anchor with the cationic head-group has also been shown to influence gene transfer activity. Substitution of the carbamate linker with either urea, an amide or amine, resulted in appreciable loss of transfection activity. PEI has been shown to be highly effective in gene transfer, which is dependent on its molecular weight and charge ratio. However, high molecular weight PEI is very toxic to the cells and tissues.

The biodegradable cationic lipopolymer of the present invention comprises a branched polyethylenimine (PEI), a cholesterol derived lipid anchor, and a biodegradable linker which covalently links the branched PEI and cholesterol derived lipid anchor. Preferably, the average molecular weight of the branched PEI is within a range of 600 to 25,000 Daltons. The branched PEI is preferably conjugated to the cholesterol derivative by an ester bond. One example of such a novel lipolymer is poly{(ethylene imine)-co-[N-2-aminoehtyl)ethylene imine]-co-[N-(N-cholesteryloxycabonyl-(2-aminoethyl))ethylene imine]} (hereafter as "PEACE"). Primary, secondary and tertiary amines of PEI contained in PEACE provide sufficient positive charges for adequate DNA condensation. The linkage between the polar head group and hydrophobic lipid anchor is biodegradable and yet strong enough to survive in a biological environment. The ester linkage between the cholesterol lipid anchor and polyethyleneimine provides for the biodegradability of the lipolymer and the relatively low molecular weight branched PEI significantly decreases the toxicity of the lipopolymer. Although a cholesterol derived lipid anchor is preferred in the present invention, other lipophilic moieties may also be used, such as $C_{12}$ to $C_{18}$ saturated or unsaturated fatty acids.

The biodegradable cationic lipopolymer of the present invention, such as PEACE, has amine group(s) which are electrostatically attracted to polyanionic compounds such as nucleic acids. The cationic lipopolymer or cationic liposome of the present invention condenses DNA, for example, into compact structures. Upon administration, such complexes of these cationic lipopolymers and nucleic acids are internalized into cells through receptor mediated endocytosis. In addition, the lipophilic group of the lipopolymer or liposome allows the insertion of the cationic amphiphile into the membrane or liposome of the cell and serves as an anchor for the cationic amine group to attach to the surface of a cell. The lipopolymers of the present invention have both highly charged positive group(s) and hydrophilic group(s), which greatly enhances cellular and tissue uptake in the delivery of genes, drugs, and other bioactive agents. In addition, using relatively low molecular weight branced PEI reduces the potential cytotoxicity of the polymer and increases transfection efficiency.

The amine groups on the branched PEI can also be conjugated either directly to the amine groups or via spacer molecules, with targeting ligands, linkers such as polyethylene glycol (PEG), and the like. PEG is an FDA-approved polymer known to inhibit the immunogenicity of molecules to which it is attached. Preferably, only a portion of the available amine groups are coupled to the ligand or spacer/ligand such that the net charge of the lipopolymer is positive. Preferably, the average molecular weight of PEG is within a range of 0.5 to 20K Daltons and more preferably within a range of 0.5 to 5K Daltons.

The target ligands conjugated to the lipopolymer direct the lipopolymer-nucleic acid/drug complex to bind to specific target cells and penetrate into such cells(tumor cells, liver cells, heamatopoietic cells, and the like). The target ligands can also be an intraellular targeting element, enabling the transfer of the nucleic acid/drug to be guided towards certain favored cellular compartments (mitochondria, nucleus, and the like). In a preferred embodiment, the ligands can be sugar moieties coupled to the amino groups. Such sugar moieties are preferably mono- or oligo-saccharides, such as galactose, glucose, fucose, fructose, lactose, sucrose, mannose, cellobiose, nytrose, triose, dextrose, trehalose, maltose, galactosamine, glucosamine, galacturonic acid, glucuronic acid, and gluconic acid.

The conjugation of an acid derivative of a sugar with the cationic lipid is most preferred. In a preferred embodiment of the present invention, lactobionic acid (4-O-β-D-galactopyranosyl-D-gluconic acid) is coupled to the lipopolymer. The galactosyl unit of lactose provides a convenient targeting molecule for hepatocyte cells because of the high affinity and avidity of the galactose receptor on these cells.

Other types of ligands that can be used include peptides such as antibodies or antibody fragments, cell receptors, growth factor receptors, cytokine receptors, transferrin, epidermal growth factor (EGF), insulin, asialoorosomucoid, mannose-6-phosphate (monocytes), mannose (macrophage, some B cells), Lewis$^x$ and sialyl Lewis$^x$ (endothelial cells), N-acetyllactosamine (T cells), galactose (colon carcinoma cells), and thrombomodulin (mouse lung endothelial cells), fusogenic agents such as polymixin B and hemaglutinin HA2, lysosomotrophic agents, nucleus localization signals (NLS) such as T-antigen, and the like.

An advantage of the present invention is that it provides a gene carrier wherein the particle size and charge density are easily controlled. Control of particle size is crucial for optimization of a gene delivery system because the particle size often governs the transfection efficiency, cytotoxicity, and tissue targeting in vivo. In general, in order to enable its effective penetration into tissue, the size of a gene delivery particle should not exceed the size of a virus. In the present invention, the particle size can be varied by using different numbers of lysinamide linked to the cholesterol, which in turn determines the particle size of the-nucleic acid complex.

In a preferred embodiment of the invention, the particle sizes will range from about 80 to 200 nm depending on the cationic lipopolymer composition and the mixing ratio of the components. It is known that particles, nanospheres, and microspheres of different sizes when injected accumulate in different organs of the body depending on the size of the particles injected. For example, particles of less than 150 nm diameter can pass through the sinusoidal fenestrations of the liver endothelium and become localized, in the spleen, bone marrow, and possibly tumor tissue after systemic administration. Intravenous, intra-arterial, or intraperitoneal injection of particles approximately 0.1 to 2.0 μm diameter leads to rapid clearance of the particles from the blood stream by macrophages of the reticuloendothelial system. The novel cationic lipopolymers of the present invention can be used to manufacture dispersions of controlled particle size, which can be organ-targeted in the manner described herein.

It is believed that the presently claimed composition is effective in delivering, by endocytosis, a selected nucleic acid into hepatocytes mediated by galactosyl receptors on the surface of hepatocyte cells. Nucleic acid transfer to other cells can be carried out by matching a cell having a selected receptor thereof with a selected sugar. For example, the carbohydrate-conjugated cationic lipids of the present invention can be prepared from mannose for transfecting macrophages, from N-acetyllactosamine for transfecting T cells, and galactose for transfecting colon carcinoma cells.

The cationic lipopolymer of the present invention provides a highly positively charged cationic lipid which is biodegradable and amphiphilic, namely hydrophilic branched PEI and hydrophobic cholesterol derivatives, where the hydrophilic polycation PEI complexes with negatively charged nucleic acids or other bioactive agents and increases the cellular uptake of drug-loaded cationic lipids. The hydrophilic group can be branched PEI where the average molecular weight of the branched PEI is within a range of 600 to 25,000 Daltons. The hydrophobic group is preferably a cholesterol or its derivative. The branched PEI is preferably conjugated with the cholesterol derivative by an ester bond. The molar ratio of the branched PEI to the conjugated cholesterol derivative is preferably within a range of 1:1 to 1:20.

By adjusting the molecular weight of the branched PEI and the molar ratio of the branched PEI to the conjugated cholesterol derivative, the resultant lipolymer can be either water soluble or water insoluble. For example, to obtain a water soluble lipopolymer of the present invention, the average molecular weight of the branched PEI is preferably within a range of 1800 to 25000, and the molar ratio of the branched PEI to the conjugated cholesterol derivative is preferably within a range of 1:1 to 1:5. To obtain a water insoluble lipopolymer of the present invention, the average molecular weight of the branched PEI is preferably within a range of 600 to 1800, and the molar ratio of the branched PEI to the conjugated cholesterol derivative is preferably within a range of 1:1 to 1:2.

The water soluable cationic lipopolymers are dispersible in water and form cationic micelles and can therefore be used to manufacture sustained release formulations of drugs without requiring the use of high temperatures or extremes of pH, and, for water-soluble drugs such as polypeptides and oligonucleotides, without exposing of the drug to organic solvents during formulations. Such biodegradable cationic lipopolymers are also useful for the manufacture of sustained, continuous release injectable formulations of drugs. They can act as very efficient dispersing agents and can be administered by injection to give sustained release of lipophilic drugs.

In addition, the water insoluble lipopolymers of the invention can be used alone, or preferably, in a mixture with a helper lipid in the form of cationic liposome formulations for gene delivery to particular organs of the human or animal body. The use of a neutral helper lipids is especially advantageous when the charge ratio (amines/phosphates) is low. Preferably the helper lipid is a member selected from the group consisting of dioleoylphosphatidylethanolamine (DOPE), oleoylpalmitoylphosphatidylethanolamin(POPE), diphytanoylphosphatidylethanolamin (diphytanoyl PE), disteroyl-, -palmitoyl-, and -myristoylphosphatidylethanolamine as well as their 1- to 3-fold N-methylated derivatives. Preferably, the molar ratio of the lipopolymer and the helper lipid is within a range of 4:1 to 1:2 and more preferably within a range of 2:1 to 1:1. To optimaze the transfection efficiency of the present compositions, it is preferred to use water as the excipient and diphytanoylPE as the helper lipid. In addition, the charge ratio (+/−) is preferably 5/1 to 1/1 for systemic delivery and 3/1 to 0.5/1 for local delivery. This ratio may be changed by a person skilled in the art in accordance with the polymer used, the presence of an adjuvant, the nucleic acid, the target cell and the mode of the administration used.

Liposomes haves been used successfully with a number of cell types that are normally resistant to transfection by other procedures. Liposomes have been used effectively to introduce genes, drugs, radiotherapeutic agents, enzymes, viruses, transcription factors, and allosteric effectors into a variety of cultured cell lines and animals. In addition, several studies suggest that the use of liposomes is not associated with autoimmune responses, toxicity or gonadal localization after systemic delivery. See, Nabel et al. Gene transfer in vivo with DNA-liposome complexes, Human Gene Ther., 3:649–656, 1992b.

Since cationic liposomes and micelles are known to be good for intracellular delivery of substances other than nucleic acids, the cationic liposomes or micelles formed by the cationic lipopolymers of the present invention can be used for the cellular delivery of substances other than nucleic acids, such as, for example, proteins and various pharmaceutical or bioactive agents. The present invention therefore provides methods for treating various disease states, so long as the treatment involves transfer of material into cells. In particular, treating the following disease states is included within the scope of this invention: cancers, infectious diseases, inflammatory diseases and genetic hereditary diseases.

The cationic lipopolymer of the present invention, having improved cellular binding and uptake of the bioactive agent to be delivered, is directed to overcome the problems associated with known cationic lipids, as set forth above. For example, the biodegradable cationic lipopolymer PEACE is easily hydrolyzed or converted to PEI and cholesterol in the body. Due to its low molecular weight, PEI will easily be released from circulaiton, where cholesterol is naturally occurring molecule. The degradation products are small, non-toxic molecules, that are subject to renal excretion and are inert during the period required for gene expression. Degradation is by simple hydrolytic and/or enzymatic reaction. Enzymatic degradation may be significant in certain organelles, such as lysosomes. The time needed for degradation can vary from days to months depending on the molecular weight and modifications made to the cationic lipids.

Furthermore, nanoparticles or microsphere complexes can be formed from the cationic lipopolymer of the present invention and nucleic acids or other negatively charged bioactive agents by simple mixing. The lipophilic group (cholesterol derivative) of the cationic lipopolymer of the present invention allows for the insertion of the cationic amphiphile into the membrane of the cell. It serves as an anchor for the cationic amine group to attach to the surface of a cell, which enhances uptake of the cationic carrier/nucleic acid complex by the cell to be transfected. Therefore, the cationic gene carrier of the present invention provides improved transfection efficiency both in vitro and in vivo, compared to known cationic gene carriers.

The following examples will enable those skilled in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

The following is the general disclosure of the sources of all the chemical compounds and reagents used in the experiments.

Polyethyleneimine (PEI) of 600, 1200 and 1800 Da was purchased from Polysciences, Inc. (Warrington, Pa.); cholesteryl-chloroformate was purchased from Aldrich, Inc. (Milwaukee, Wis.); 2-dioleoyl-sn-glycero-3-phosphoethanolamine (DOPE) was purchased from Avanti Polar Lipids (Alabaster, Ala.). Triethylamine (TEA); anhydrous methylene chloride; chloroform; ethyl ether, and acetone were purchased from Sigma (St. Louis, Mo.).

EXAMPLE 1

Synthesis of Water-Insoluble PEACE

This example illustrates the preparation of water-insoluble PEACE.

One gram of PEI (Mw: 1200 Daltons) was dissolved in a mixture of 15 mL anhydrous methylene chloride and 100 µl triethylamine (TEA). After stirring on ice for 30 minutes, 1.2 g of cholesteryl chloroformate solution was slowly added to the PEI solution and the mixture was stirred overnight on ice. The resulting product (PEACE) was precipitated by adding ethyl ether followed by centrifugation and subsequent washing with additional ethyl ether and acetone. PEACE was dissolved in chloroform for a final concentration of 0.08 g/mL. A schematic of the above reaction is presented in FIG. 1. Following synthesis and purification, PEACE was characterized using MALDI-TOFF MS and $^1$H NMR.

Figure 2A:
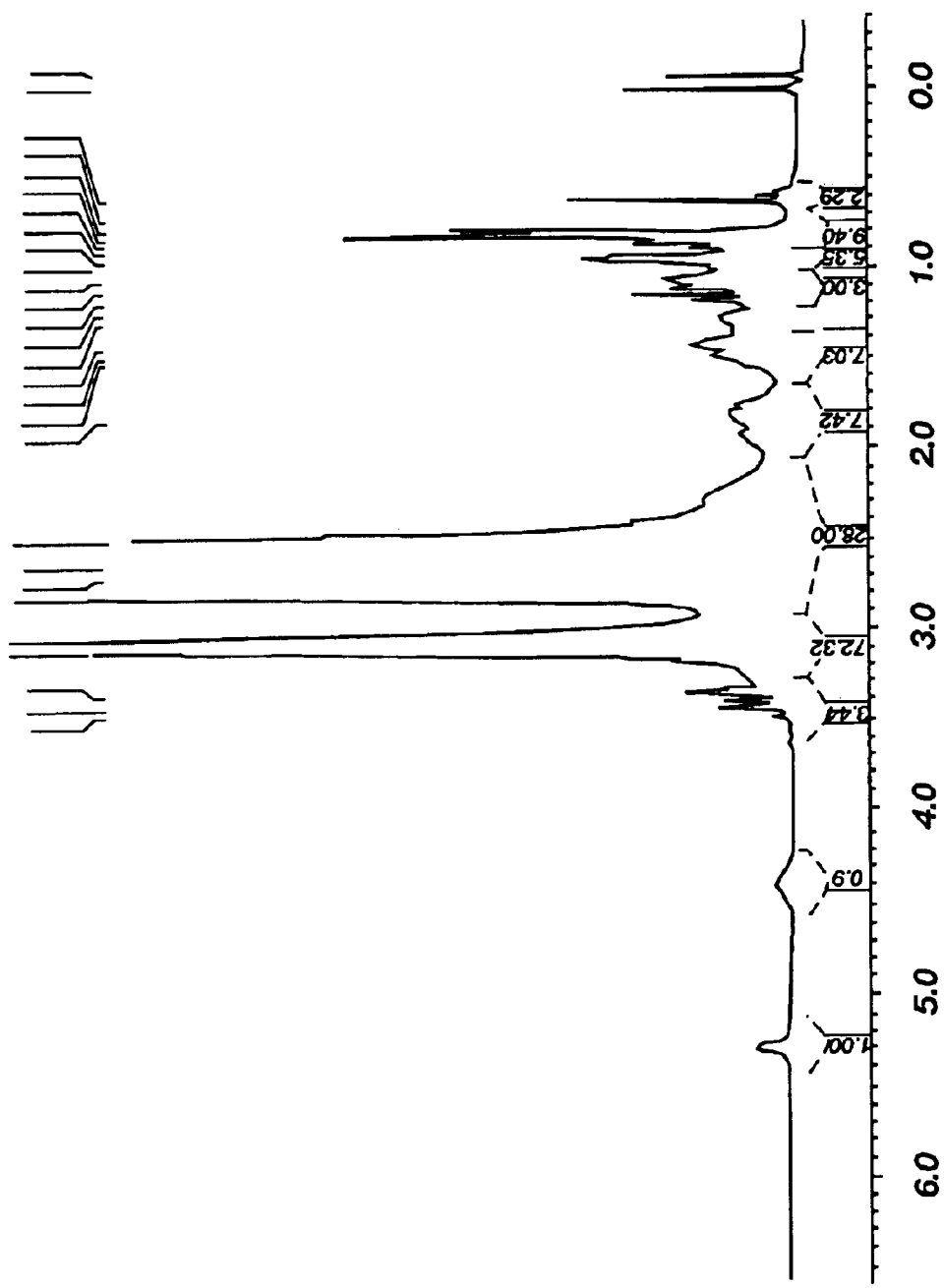
FIG. 2. illustrates determination of chemical structure and molecular weight of water insoluble PEACE 1800 by $^1$H NMR spectra(FIG. 2A) and MALDI-TOF mass spectra(FIG. 2B).
Figure 2B:
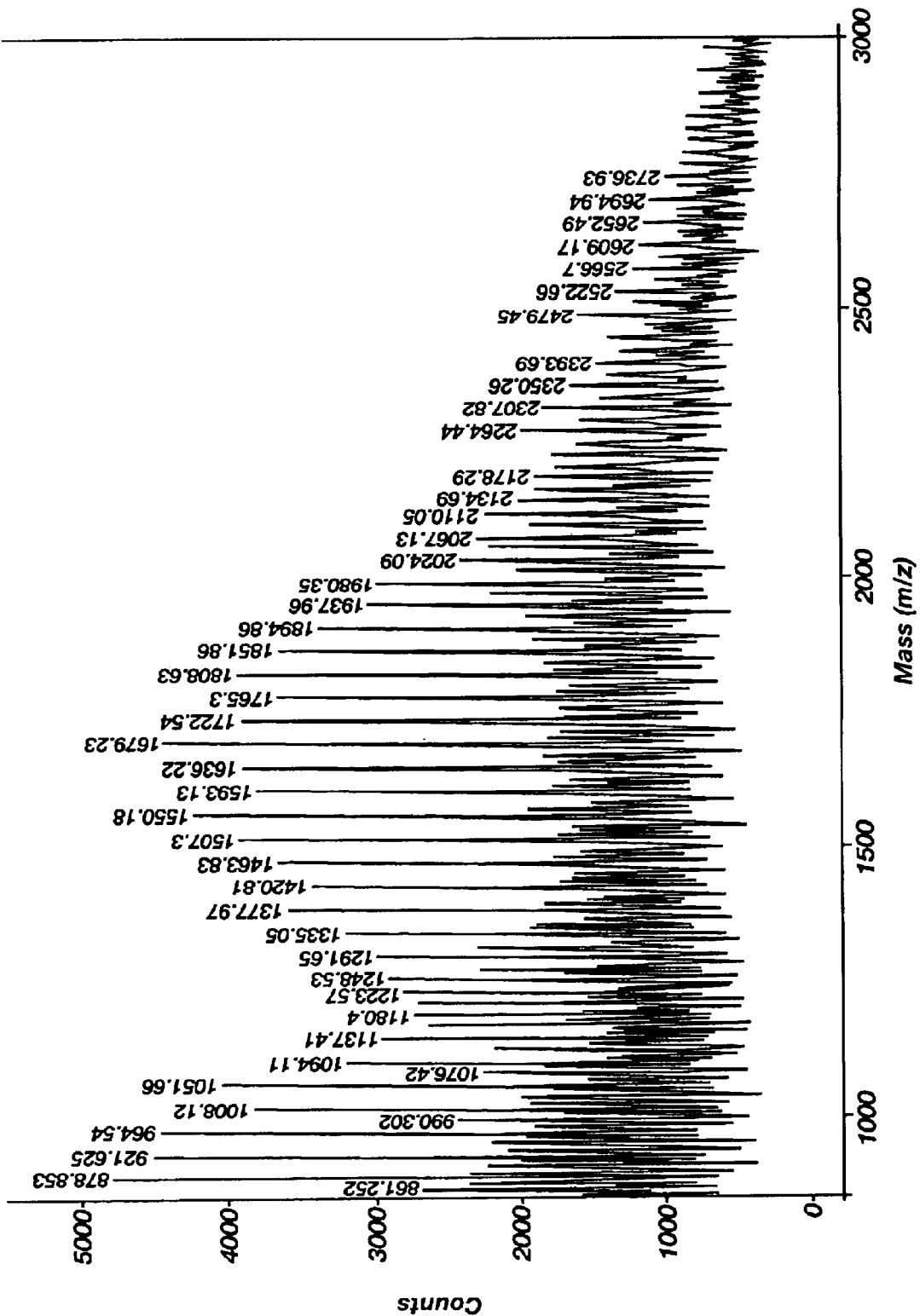

The NMR results of water insoluble PEACE 1200 are as follows: as illustrated in FIG. 2A, $^1$H NMR (200 MHz, CDCl$_3$), δ0.6 (3 H of CH$_3$ from cholesterol); δ2.5 (230 H of —NHCH$_2$CH$_2$— from the backbone of PEI); δ3.1 (72 H of =N—CH$_2$CH$_2$—NH$_2$ from the side chain of PEI); δ5.3 (1 H of =C=CH—C— from cholesterol). Another peak appearing at δ0.8, −δ1.9 was cholesterol. The amount of cholesterol conjugated to PEI was determined to be about 40%. MALDI-TOF mass spectrometric analysis of PEACE showed its molecular weight to be approximately 1600, as illustrated in FIG. 2B. The peak appeared from 800 to 2700 and the majority peaks were around 1600, which is expected since PEI of 1200 Da and cholesterol of 414 (removal of chloride) were used for synthesis. This suggests that the majority of PEACE 1200 synthesized were of 1/1 molar ratio of cholesterol and PEI, although some were either not conjugated or conjugated at the molar ratio of 2/1 (cholesterol/PEI).

EXAMPLE 2

Synthesis of Water Soluble PEACE

This example illustrates the preparation of water-soluble PEACE.

Three grams of PEI (Mw: 1800 Daltons) was stirred on ice in a mixture of 10 ml anhydrous ethylene chloride and 100 µl triethyamine for 30 minutes. One gram of cholesterol chloroformate was dissolved in 5 ml of anhydrous ice-cold methylene chloride and then slowly added to the PEI solution for 30 minutes. The mixture was stirred for 12 hrs on ice and the resulting product was dried in a rotary evaporator. The powder was dissolved in 50 ml 0.1 N HCl. The aqueous solution was extracted with 100 mL of methylene chloride 3 times, and then filtered through a glass microfiber filter. The product was concentrated by solvent evaporation, precipitated with large excess acetone, and dried under vacuum. The product was analyzed using MALDI-TOF mass spectrophotometry and $^1$H NMR and then stored at −20° C. until used.

Figure 3A:
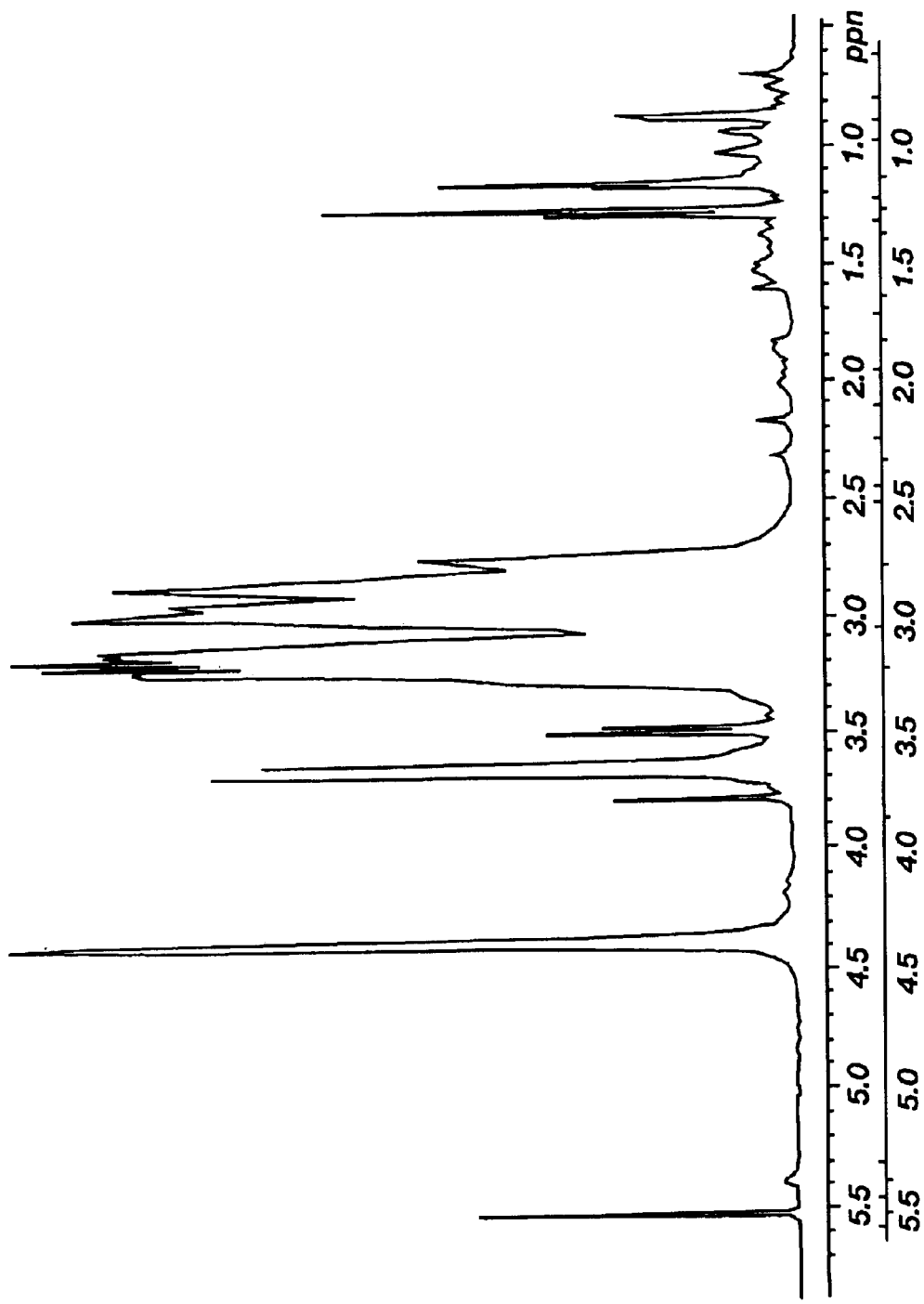
FIG. 3 illustrates determination of chemical structure and molecular weight of water soluble PEACE 1800 by $^1$H NMR spectra(FIG. 3A) and MALDI-TOF mass spectra(FIG. 3B).
Figure 3B:
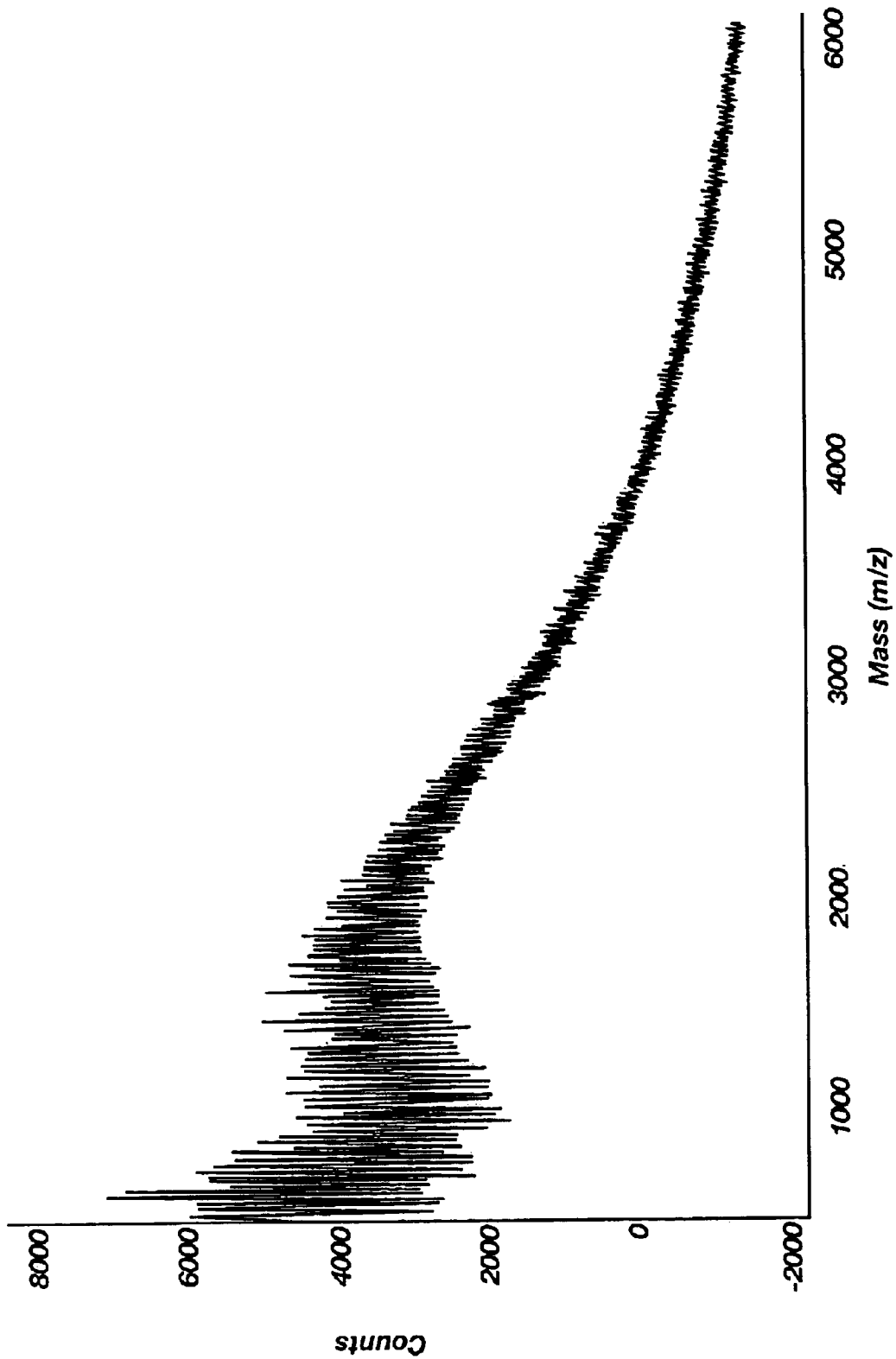

The NMR results of water soluble PEACE 1800 are as follows:as illustrated in FIG. 3A, $^1$H NMR (500 MHz, D$_2$O+1,4-Dioxane-d$_6$), δ0.8 (2.9 H of CH$_3$ from cholesterol); δ2.7 (59.6 H of —NHCH$_2$CH$_2$— from the backbone of PEI); δ3.2 (80.8 H of =N—CH$_2$CH$_2$—NH$_2$ from the side chain of PEI); δ5.4 (0.4 H of =C=CH—C— from cholesterol). Another peak appearing at δ0.8, −δ1.9 was cholesterol. The amount of cholesterol conjugated to PEI was determined to be about 47%. MALDI-TOFF mass spectrometric analysis of PEACE showed its molecular weight to be approximately 2200. The peak appeared from 1000 to 3500 and the majority peaks were around 2200, as illustrated in FIG. 3B. Expected position is 2400, one chloride 35 is removed from PEI 1800+cholesteryl chloroformate 449. This suggests that the majority of PEACE 1800 synthesized were of 1/1 molar ratio of cholesterol and PEI, although some were either not conjugated or conjugated at the molar ratio of 2/1 (cholesterol/PEI).

EXAMPLE 3

Synthesis of PEACE Using Secondary Amine Group

Fifty microliters of PEI was dissolved in 2 mL of anhydrous methylene chloride on ice. Then, 200 µL of benzyl chloroformate was slowly added to the reaction mixture and the solution was stirred for 4 hours on ice. Following stirring, 10 mL of methylene chloride was added and the solution was extracted with 15 mL of saturated NH$_4$Cl. Water was removed from methylene chloride phase using magnesium sulfate. The solution volume was reduced under vacuum and the product (called CBZ protected PEI) was precipitated with ethyl ether. Fifty micrograms of primary amine CBZ protected PEI was dissolved in methylene chloride, 10 mg of cholesterol chloroformate was added, and the solution was stirred for 12 hours on ice. The product (CBZ protected PEACE) was precipitated with ethyl ether, washed with acetone, and then dissolved in DMF containing palladium activated carbon as catalyst under H$_2$ as hydrogen donor. The mixture was stirred for 15 hours at room temperature, filtered with Celite®, and the solution volume was reduced by rotatory evaporator. The product was finally obtained from precipitation with ethyl ether.

EXAMPLE 4

Synthesis of Glycosylated PEACE

Two hundred milligrams of PEI was glycosylated using 8 mg of α-D-glucopyranosyl phenylisothiocyanate dissolved in DMF. To synthesize galactosylated, mannosylated and lactosylated PEACE, α-D-galactopyranosyl phenylisothiocyanate, α-D-mannopyranosyl phenylisothiocyanate, α-D-lactopyranosyl phenylisothiocyanate were used, respectively. The solution was adjusted to pH 9 by addition of 1 M $Na_2CO_3$ and incubated for 12 hrs at room temperature. The glucosylated PEI was dialyzed against 5 mM NaCl for 2 days. The volume of the resulting materials were reduced under vacuum and precipitated with acetone. The dried (under $N_2$) mannosylated PEI was dissolved in methylene chloride and reacted with cholesteryl chloroformate as described in Example 2.

EXAMPLE 5

Synthesis of Folate PEACE Conjugation

Two hundred milligrams of PEI was conjugated with 10 mg of folic acid dissolved in dimethylsulfoxide (DMSO) containing 1,3-Dicyclohexylcarbodiimide (DCC). After 12 hours with stirring, the product (Folate-PEI) is purified with FPLC. The solution was dialyzed against deionized water for 2 days. The volume of the resultant materials were reduced under vacuum and precipitated with acetone. The result materials were dried under $N_2$. The dried folate PEI was dissolved in methylene chloride and reacted with cholesteryl chloroformate as described in Example 2.

EXAMPLE 6

Synthesis of RGD PEACE Conjugation

We use cyclic $NH_2$-Cys-Arg-Gly-Asp-Met-Phe-Gly-Cys-CO—$NH_2$ as an RGD peptide with an N-terminus. RGD peptide was synthesized using solid phase peptide synthetic methods with F-moc chemistry. Cyclization was performed using 0.01M $K_3[Fe(CN)_6]$ in 1 mM $NH_4OAc$ at pH 8.0 overnight at room temperature and then purified with HPLC. One molar N-terminal amine group of RGD peptide was reacted with 2 mol N-succinimidyl 3 (2-pyridyldithio) propionate (SPDP) in DMSO and precipitated with ethyl-ether (RGD-PDP). Two hundred milligrams of PEI was reacted with 7 milligrams of SPDP in DMSO for 2 hrs at room temperature. The resulting materials (PEI-PDP) were treated with 0.1 M (–)1,4-Dithio-L-threitol (DTT) followed by separation bio-spin column. RGD-PDP was dissolved in DMF and then added to PEI-PDP solution. After 12 hrs stirring, the resulting material (RGD-PEI) was purified by FPLC. The resulting solution was dialyzed against deionized water for 2 days followed by reducing volume using a rotary evaporator. The resulting materials were precipitated with a large excess of acetone. Dried RGD-PEI was reacted with cholesteryl chloroformate as described in Example 2.

EXAMPLE 7

Preparation of Liposomes

PEACE and DOPE were dissolved in methylene chloride at molar ratios of 1/1, 1/2 and 2/1 and then added to a 100-mL round-bottomed flask. The clear solution was rotated on a rotary evaporator at 30° C. for 60 min, resulting in thin translucent lipid films. The flasks were covered with punctured-para-film and the lipid film was dried overnight under vacuum. The films were hydrated in 5 mL sterile water to give a final concentration of 5 mM for PEACE. The hydrated films were vortexed for 60 min and extruded through 0.4 μm pore size polycarbonate filters using a 10-mL extruder (Lipex Biomembranes, Inc., Vancouver, BC).

EXAMPLE 8

Amplification and Purification of Plasmids

This example illustrates the preparation of DNA to be complexed with the liposome prepared in Example 7. Plasmid pCMV-Luciferase (pCMV-Luc) was used as a reporter gene and pmIL-12(a plasmid carrying the murine interleukin-12, or mIL-12 gene) as a therapeutic gene. The p35 and p40 sub-units of mIL-12 were expressed from two independent transcript units, separated by an internal ribosomal entry site (IRES), and inserted into a single plasmid, pCAGG. This vector encodes mIL-12 under the control of the hybrid cytomgalovirs induced enhancer (CMV-IE) and chicken β-actin promoter. All plasmids were amplified in *E. coli* DH5α strain cells, and then isolated and purified by QIAGEN EndoFree Plasmid Maxi Kits (Chatsworth, Calif.). The plasmid purity and integrity was confirmed by 1% agarose gel electrophoresis, followed by ethidium bromide staining, the pDNA concentration was measured by ultraviolet (UV) absorbance at 260 nm.

EXAMPLE 9

Preparation of Water Soluble PEACE/pDNA and PEACE:DOPE/pDNA Complexes

This example illustrates the formation of water soluble PEACE/pcDNA and PEACE:DOPE/pDNA complexes.

The water soluble PEACE prepared in Example 2, the PEACE:DOPE liposomes prepared in Example 7, and the pDNA prepared in Example 8 were diluted separately with 5% glucose to a volume of 250 μl each, and then the pDNA solution was added to the liposomes under mild vortexing. Complex formation was allowed to proceed for 30 minutes at room temperature. To study the effect of charge ratio on gene transfer, water soluble PEACE/pcDNA and PEACE:DOPE/pDNA complexes were prepared at charge ratios range from 1/1 to 5/1(+/–). Following complex formation, osmolality and pH of PEACE:DOPE/pDNA complexes were measured. The results are shown in Table 1.

The water soluble PEACE/pDNA and PEACE:DOPE liposomes/pDNA complexes formulated at several charge ratios were diluted 5 times in the cuvette for the measurement of particle size and ζ potential of the complexes. The electrophoretic mobility of the samples was measured at 37° C., pH 7.0 and 677 nm wavelength at a constant angle of 15° with ZetaPALS (Brookhaven Instruments Corp., Holtsville, N.Y.). The zeta potential was calculated from the electrophoretic mobility based on Smoluchowski's formula. Following the determination of electrophoretic mobility, the samples were subjected to mean particle size measurement.

The mean particle size of water soluble PEACE/pDNA complexes was much smaller than that of PEACE:DOPE/pDNA formulated at 3/1 (+/–) ratio in 5% glucose (42 nm vs. 221 nm). Overall, these complexes had a narrow particle size distribution. In case of PEACE:DOPE liposome/pDNA complexes, there was decrease in particle size with increase in the charge ratios: 430, 221 and 193 nm at 1/1, 3/1 and 5/1 (+/–) charge ratios, respectively.

TABLE 1

Physicochemical properties of water soluble PEACE/pDNA and PEACE:DOPE liposomes/pDNA complexes.

|  | Particle Size (nm) | Zeta Potential (mV) | Osmolality (mOsm/kg) | pH |
|---|---|---|---|---|
| Water Soluble PEACE | | | | |
| PEACE 1800/pDNA (1/1, +/–) | 100.6 ± 1.5 | 8.23 ± 0.25 | ~300 | |
| PEACE 1800/pDNA (3/1, +/–) | 42.1 ± 0.35 | 37.40 ± 0.46 | ~300 | |

TABLE 1-continued

Physicochemical properties of water soluble PEACE/pDNA and PEACE:DOPE liposomes/pDNA complexes.

| | Particle Size (nm) | Zeta Potential (mV) | Osmolality (mOsm/ kg) | pH |
|---|---|---|---|---|
| PEACE 1800/pDNA (5/1, +/−) Water Insoluble PEACE | 61.8 ± 0.1 | 61.67 ± 0.62 | ~300 | |
| PEACE 1200:DOPE (1/1)/ pDNA (1/1, +/−) | 430.6 ± 12.5 | 8.46 ± 0.4 | ~310 | 7.2~ 7.6 |
| PEACE 1200:DOPE (1/1)/ pDNA (3/1, +/−) | 220.8 ± 8.4 | 34.73 ± 0.7 | ~310 | 7.2~ 7.6 |
| PEACE 1200:DOPE (1/1)/ pDNA (5/1, +/−) | 193.3 ± 6.9 | 47.00 ± 0.7 | ~310 | 7.2~ 7.6 |

The zeta potential of these complexes was in the range of 8 to 47 mV, and increased with increase in charge ratios (+/−). The osmolality of these complexes was in the range of 331–359 mOsm, whereas that of the complexes formulated in 4% glucose was about 310 mOsm.

EXAMPLE 10

Gel Retardation and DNase Protection Assays

Figure 4A:
FIG. 4 illustrates gel retardation assay of water soluble PEACE/pCMV-Luc complexes (FIG. 4A) and PEACE:DOPE liposome/pCMV-Luc complexes (FIG. 4B).
Figure 4B:
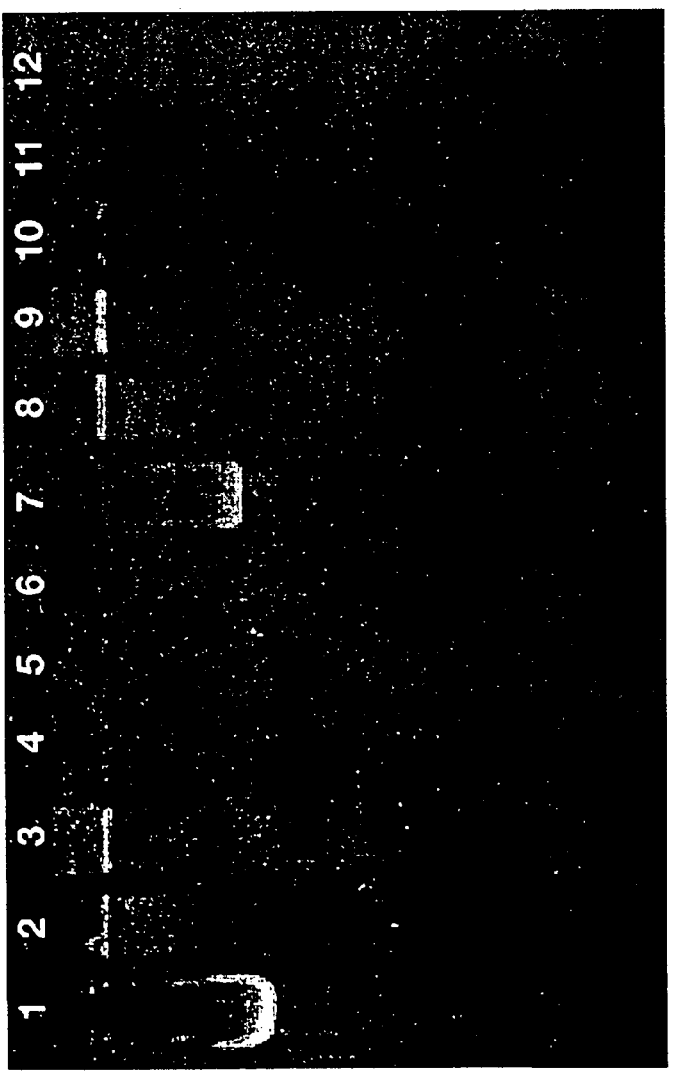

The ability of water soluble PEACE and water insoluble PEACE:DOPE liposomes to condense and protect pDNA from enzymatic degradation was evaluated in this Example. Briefly, water soluble PEACE and PEACE:DOPE liposomes were complexed with pDNA at various charge ratios (+/−) ranging from 0.5/1 to 5/1 in the presence of 5% glucose (w/v) glucose to adjust the osmolality at 290~300 mOsm. The complexes were electrophoresed on a 1% agarose gel. As illustrated in FIG. 4A and FIG. 4B, the positively charged PEACE makes strong complexes with the negatively charged phosphate ions on the sugar backbone of DNA. When the charge ratio(+/−) reached 1/1, no free DNA was seen.

The ability of water soluble PEACE and PEACE:DOPE liposomes to protect pDNA from enzymatic degradation was assessed by a DNase protection assay. Twenty micrograms of pDNA was complexed with water soluble PEACE or PEACE:DOPE liposomes at various charge ratios and incubated at ambient conditions for 30 minutes. DNase I (273 units) were added to the formulations and the samples were incubated at 37° C. for a defined period. At 0, 5, 15, and 60 min post-incubation, 50 μl samples were taken into Eppendorf tubes and mixed with 50 μl of 100 mM EDTA under mild vortexing to inactivate DNase. Heparin (162 units/mg DNA) were added to dissociate the pDNA from the water soluble PEACE or PEACE:DOPE liposomes. Heparin was allowed to react with the mixtures for 20 minutes, and then the samples were loaded onto a 1% agarose gel for electrophoresis.

Figure 5:
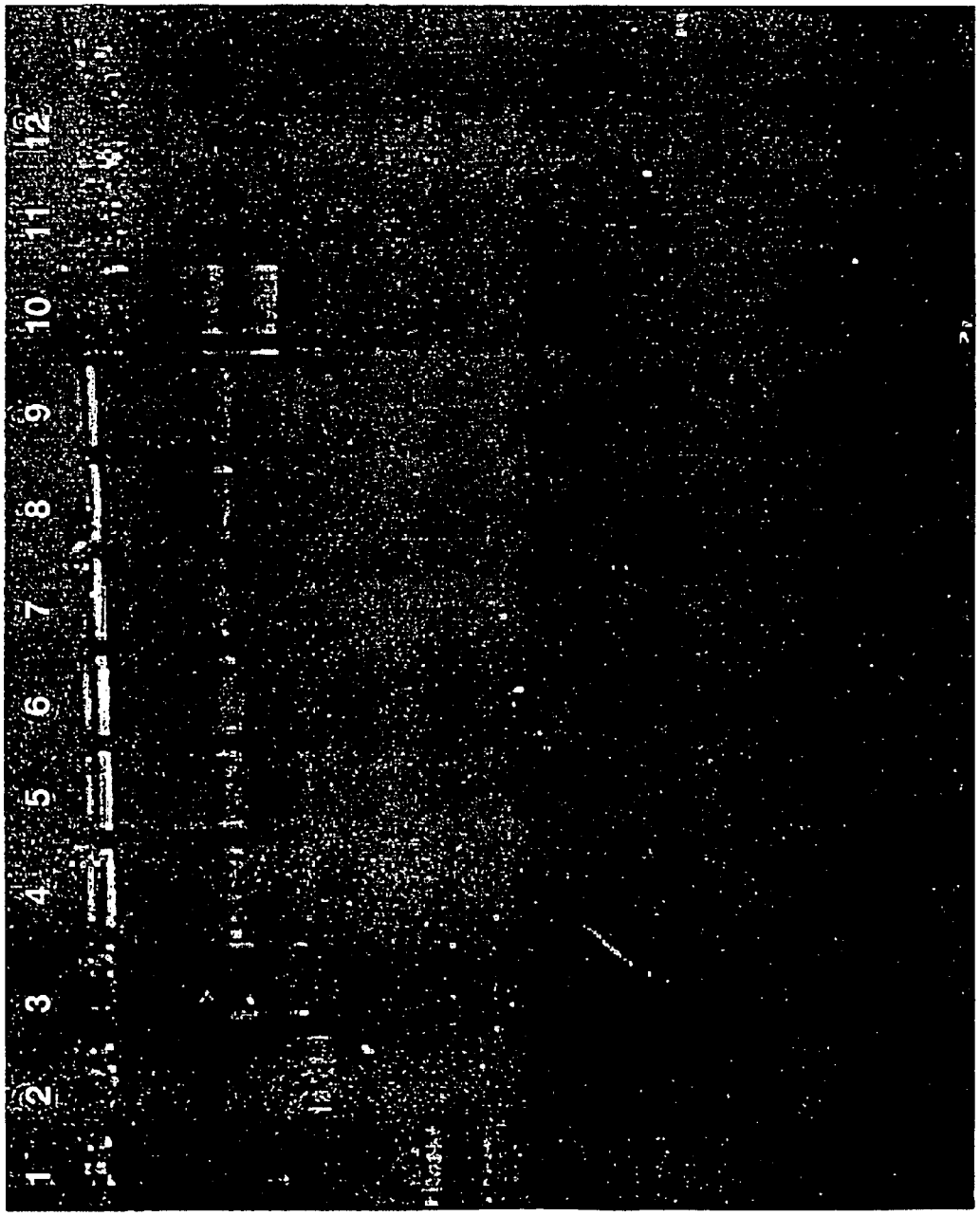
FIG. 5 illustrates Dnase protection assay of water soluble PEACE/pCMV-Luc complexes.

Both water soluble PEACE and PEACE:DOPE liposomes could protect plasmids from degradation by nucleases up to 60 min post-incubation in the presence of DNase at a 3/1 (+/−) charge ratio. FIG. 5 illustrates that water soluble PEACE could protect DNA even after incubation at 37° C. for 2 hrs. Plasmid DNA when complexed with PEACE-:DOPE.liposomes at charge ratio of 3/1 (+/−), was completely condensed and formed spherical particles. The particle size of these complexes was about 200~300 nm(Table 1). Even though there is limited understanding of the cellular mechanism in the lipid-mediated gene transfer, complex formation at the level of nanometer scale is generally considered to be a prerequisite for entry of lipid/DNA complexes into cells.

EXAMPLE 11

Cytotoxicity

This example illustrates water soluble PEACE/pCMV-Luc and PEACE:DOPE liposoemes/pCMV-Luc complexes being tested for cytotoxicity using a MTT assay in CT-26 cells over a wide range of charge ratios. MTT colorimetric assay as originally described by T. Mosmann, Rapid Colorimetric Assay for Cellular Growth and Survival: Application to Proliferation and Cytotoxicity Assays, 65 J. Immunol. Methods 55–63 (1983), hereby incorporated by reference.

CT-26 murine colon adenocarcinoma cells were grown and maintained in RPMI 1640 medium supplemented with 10% fetal bovine serum (FBS), 100 U/mL penicillin, 100 U/mL streptomycin, and 50 μg/mL gentamycin at 37° C. and humidified 5% $Co_2$.

CT-26 cells were seeded in a 96-well plate with RPMI (10% FBS) at 4,000/cells per well and incubated (37° C., 5% $CO_2$) overnight. After reaching 80% confluency, 0.64 μg pDNA were added at various water soluble PEACE/pDNA or PEACE:DOPE/pDNA charge ratios and incubated (37° C., 5% $CO_2$) for 48 hours. Following incubation, 25 μl of 3-[4,5-dimethylthiazol-2-yl]-2,5-diphenyltetrazolium bromide (MTT) stock solution in phosphate buffered saline were added to each well with a final concentration of 0.5 mg/mL MTT per well. The plate was incubated for an additional 4 hours. The media was removed and 150 μl DMSO were added to dissolve the formazan crystals. The plate was spectrophotometrically read at 570 nm on an ELISA plate reader. The relative cell (%) was calculated according to the following equation:

Viability (%)=[$OD_{570}$(sample)/$OD_{570}$ (control)]×100 where the $OD_{570}$ (control) represents the measurement from the wells treated with PBS buffer only and the $OD_{570}$ (sample) represents the measurement from the wells treated with varying amounts of PEACE:DOPE/pDNA at various charge ratios.

Figure 6A:
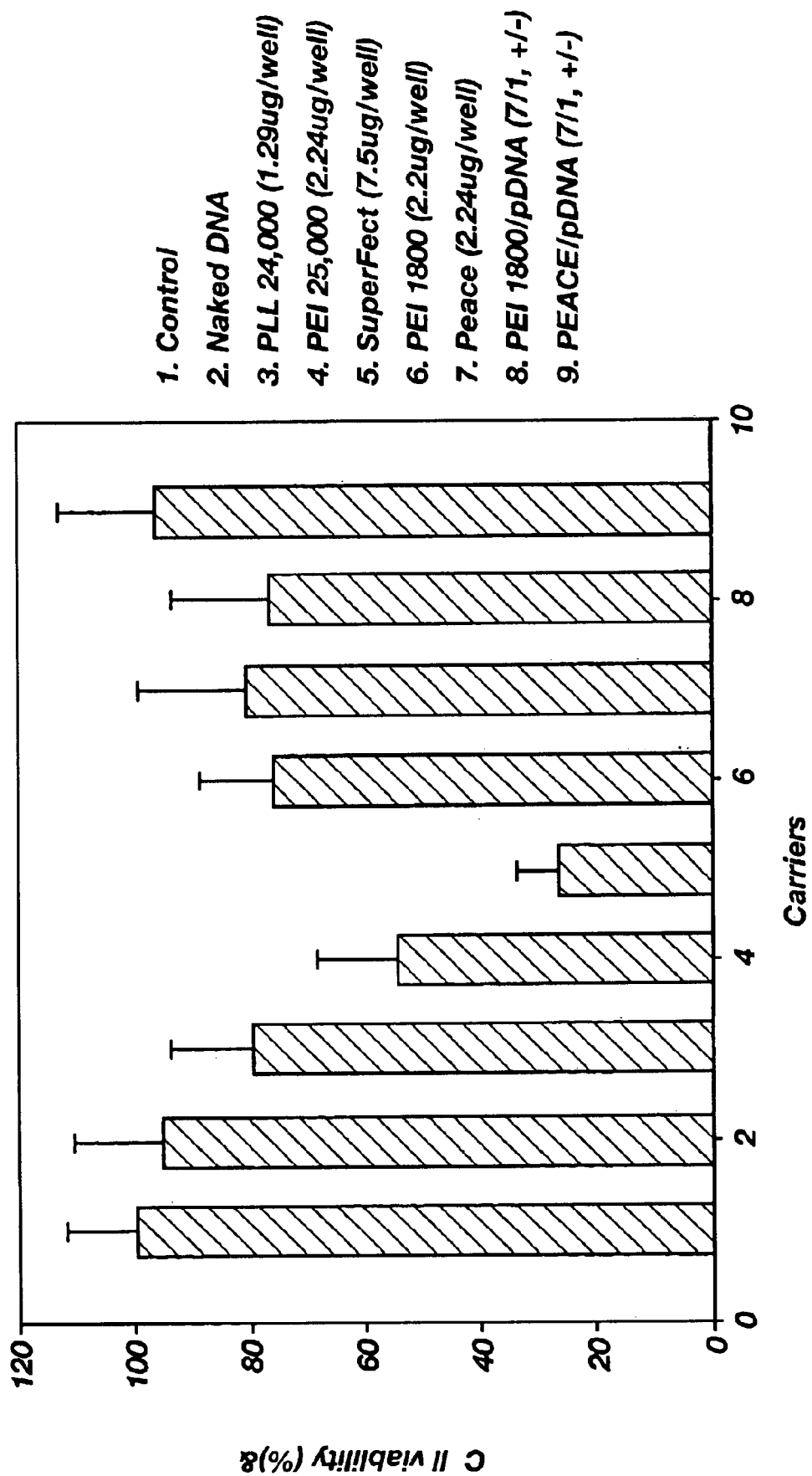
FIG. 6 illustrates viability assay of CT-26 colon adenocarcinoma cells after being transfected by water soluble PEACE/pCMV-Luc complexes (FIG. 6A) and PEACE:DOPE liposome/pCMV-Luc complexes (FIG. 6B).
Figure 6B:
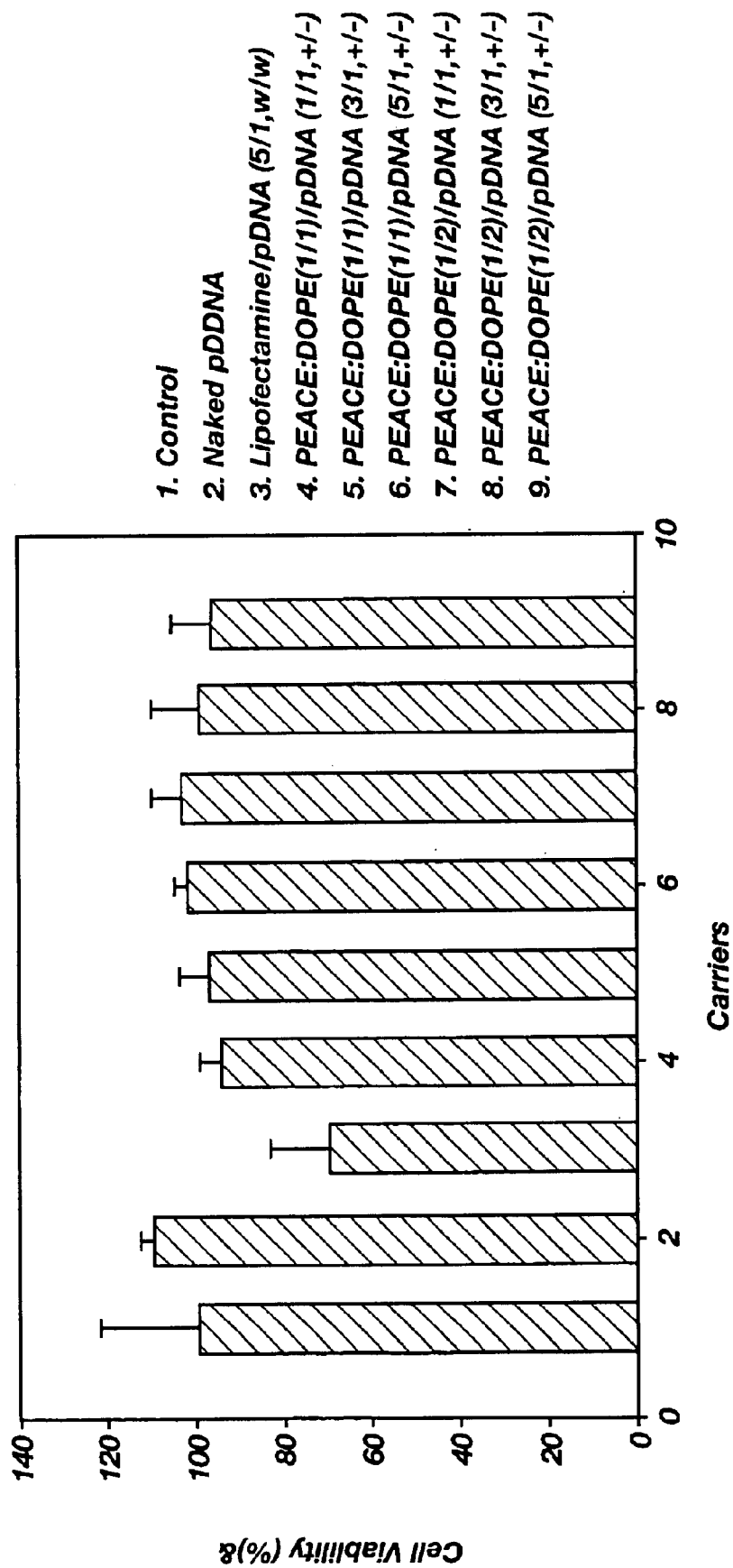

Commercially available cationic liposomes (LipofectAMINE)/pCMV-Luc complexes (5/1, w/w) and poly(L-lysine)(PLL) were used for comparison. LipofectAMINE reagent is a 3:1 (w/w) liposome formulation of the polycationic lipid 2,3-dioleyloxy-N-[2 (sperminecarboxamido)ethyl]-N,N-dimethyl-1-propanaminium trifluoroacetate (DOSPA) (MW 867) and the neutral lipid dioleoyl phosphatidylethanolamine (DOPE) (MW 744) in membrane filtered water. Based on its chemical structure LipofectAMINE has 2 primary amines, 2 secondary amines and 1 quaternary amine, totaling 5 positive charges per molecule. Subsequent calculations show that 5/1 (w/w) corresponds to 6.823/1 (+/−) for LipofectAMINE/pDNA complexes. Following normalization by (+/−) charge ratios, we thus confirmed that water soluble PEACE/pDNA complexes prepared at 7/1 (+/−) charge ratio were not toxic to cells, whereas both PEI (mw 25000 Daltons) and Superfect were toxic to the cells, as illustrated in FIG. 6A. Similarly, PEACE:DOPE liposomes/pCMV-Luc complexes were less toxic to the cells when formulated at the charge ratio of 7/1 (+/−) and below. In contrast, LipofectAMINE/pCMV-Luc complexes were very toxic to the cells, as illustrated in FIG. 6B.

An important feature of the cationic lipopolymer of the present invention is its relatively low toxicity toward the cells at concentrations required for optimal transfection, for cytotoxicity is one of the major barriers in the application of many cationic amphiphiles. The toxicity of some of the commercially available cationic lipids and synthetic polycationic polymers, such as: Lipofectin and PEI, has been attributed to their non-natural, non-biodegradable nature. The results suggest that the natural properties and biodegradabiity of the lipopolymer of the present invention result in the low cytotoxicity and improved biocompatibility.

EXAMPLE 12

In Vitro Transfection

In this example, water soluble PEACE/pCMV-Luc, PEACE:DOPE liposomes/pCMV-Luc and PEACE:DOPE liposomes/pmIL-12 complexes formulated at different charge ratios in 5% (w/v) glucose were evaluated for their transfection efficiency in CT-26 colon carcinoma cell lines.

Figure 7A:
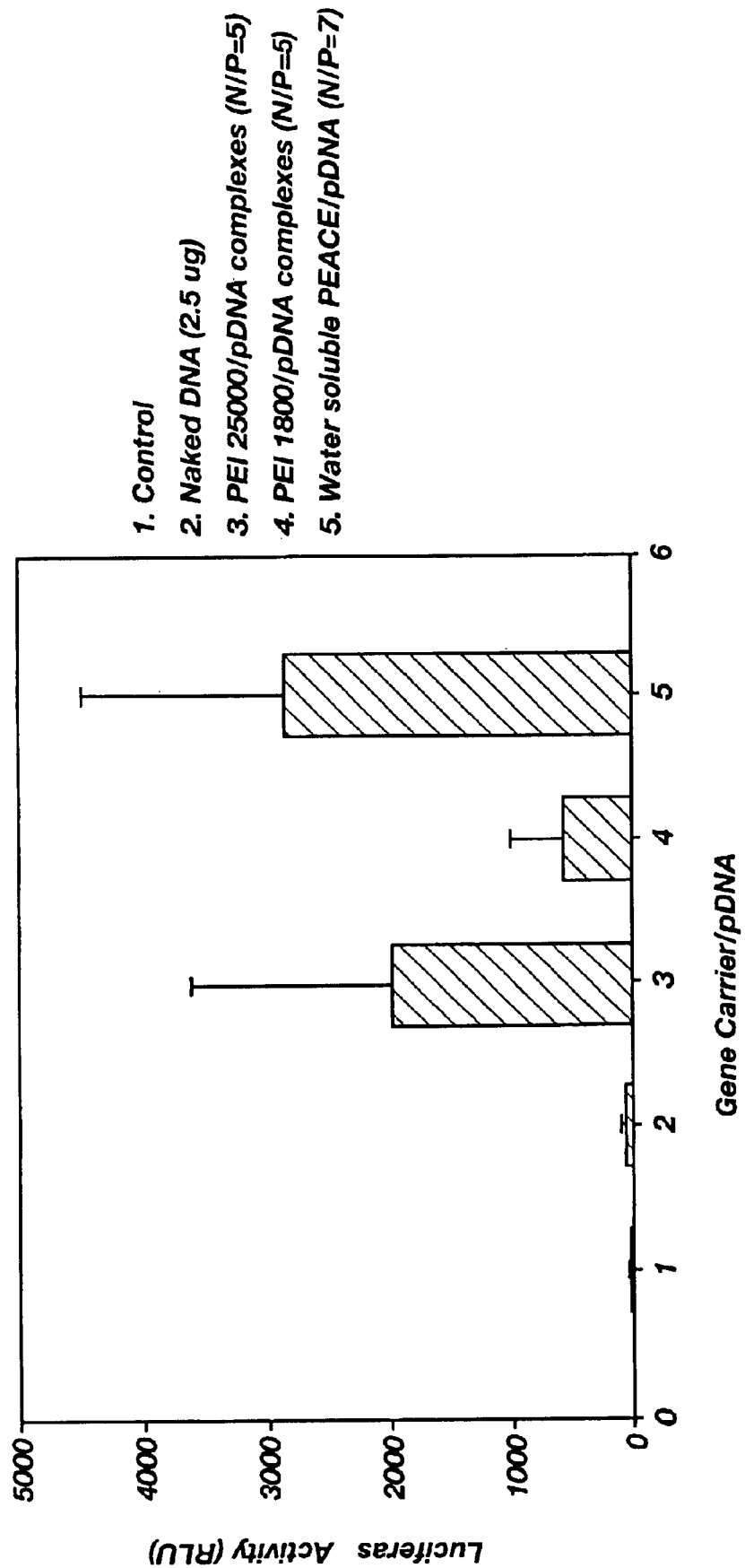
FIG. 7 illustrates luciferase activity assay in cultured CT-26 colon adenocarcinoma cells after being transfected by water soluble PEACE/pCMV-Luc complexes (FIG. 7A) and PEACE:DOPE liposome/pCMV-Luc complexes (FIG. 7B).
Figure 7B:
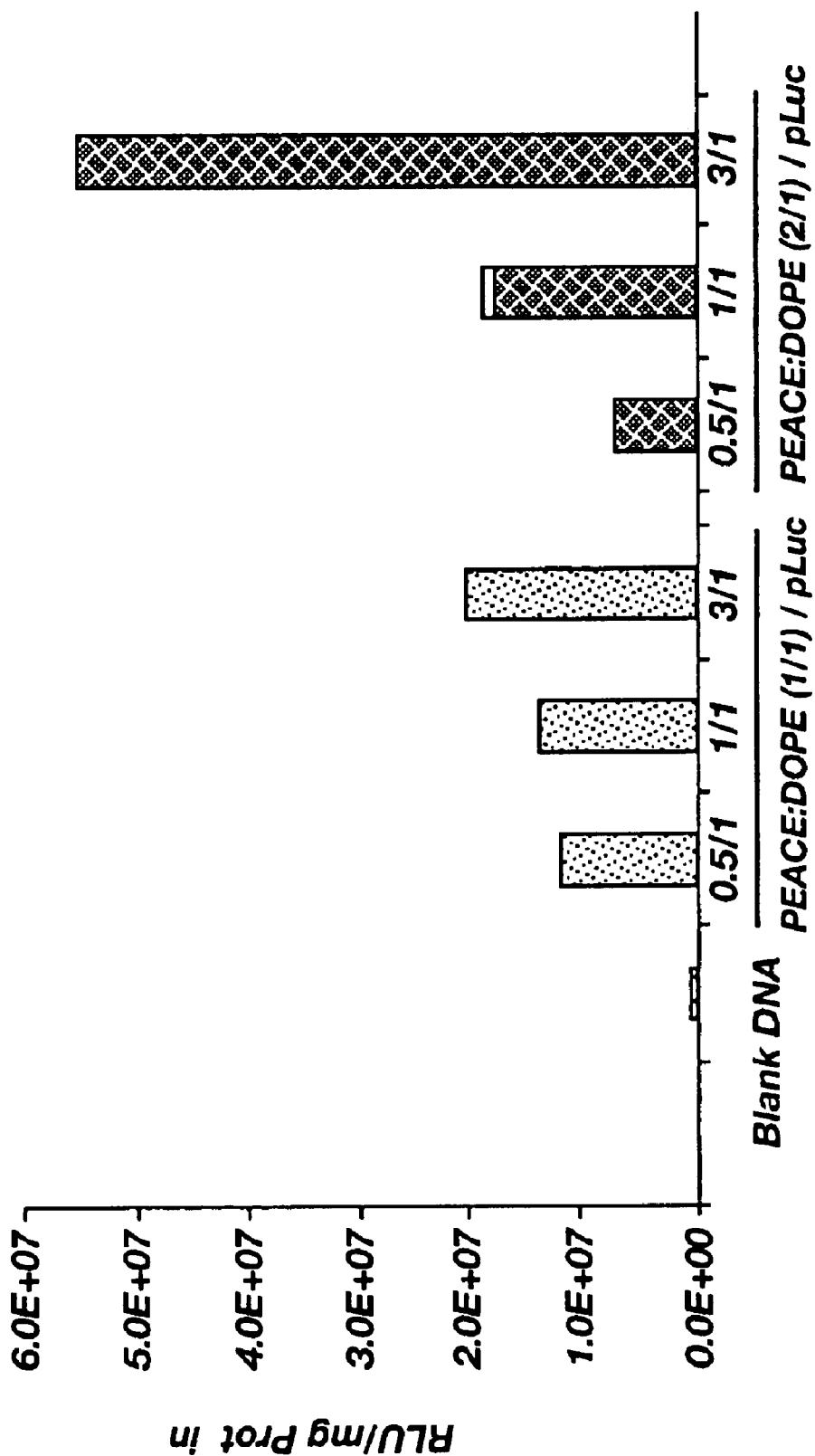

In the case of luciferase gene, CT-26 cells were seeded in six well tissue culture plates at $4\times10^5$ cells per/well in 10% FBS containing RPMI 1640 media. Cells achieved 80% confluency within 24 hours after which they were transfected with water soluble PEACE/pDNA or PEACE:DOPE liposomes/DNA complexes prepared at different charge ratios ranging from 0.5/1(+/−) to 0.5/1 to 5/1 (+/−) charge ratios. The total amount of DNA loaded was maintained constant at 2.5 µg/well and transfection was carried out in absence of serum. The cells were incubated in the presence of complexes for 5 hours in $CO_2$ incubator followed by replacement of 2 ml of RPMI 1640 containing 10% FBS and incubation for additional 36 hours. Cells were lysed using 1× lysis buffer (Promega, Madison, Wis.) after washing with cold PBS. Total protein assays were carried out using BCA protein assay kit (Pierce Chemical Co, Rockford, Ill.). Luciferase activity was measured in terms of relative light units (RLU) using 96 well plate Luminometer (Dynex Technologies Inc, Chantilly, Va.). The final values of luciferase were reported in terms of RLU/mg total protein. Both naked DNA and untreated cultures were used as positive and negative controls, respectively. As illustrated in FIG. 7A, the transfection efficiency of water soluble PEACE was higher than PEI. In case of PEACE:DOPE liposome/pDNA complexes, the transfection efficiency was dependent on the charge ratio and PEACE/DOPE molar ratios and was the highest for PEACE:DOPE (2/1 mol/mol) liposomes/pCMV-Luc complexes, as illustrated in FIG. 7B.

In case of mIL-12 gene, CT-26 cells were seeded in 75 $cm^2$ flasks at $2\times10^6$ cells/flask in 10% FBS containing RPMI 1640. Cells achieved 80% confluency in 24 hours after which they were transfected with PEACE:DOPE liposomes/pmIL-12 complexes prepared at different charge ratios ranging from 0.5/1 (+/−) to 5/1 (+/−). The total amount of DNA loaded was maintained at 15 µg/flask and transfection was carried out in absence of serum. The cells were allowed to incubate in the presence of the complexes for 5 hours in a $CO_2$ incubator followed by replacement of 10 ml of RPMI 1640 containing 10% FBS. Thereafter the cells were incubated for additional 36 hours. Culture supernatants were assayed for mIL-12 p70 and p40 using enzyme linked immunosorbent assay (ELISA) kits as suggested by the manufacturer. Results similar to luciferase transfection were found when a gradient of various charge ratios was used. The mIL-12 levels for PEACE:DOPE liposomes/pmIL-12 complexes (3/1, +/−) were substantially higher than naked pmIL-12 or non-transfected samples.

To complement the ELISA results of in vitro transfected samples, reverse transcriptase polymerase chain reaction (RT-PCR) was performed to detect mRNA transcripts for mIL-12 in transfected tumor cells. Following transfection, total RNA was isolated using RNeasy Qiagen kit (Qiagen Inc., Valancia, Calif.). Samples were lysed and homogenized in the presence of guanidine isothiocynate and then reverse transcribed using OmniscriptTM reverse transcriptase kit (Qiagen, Valencia, Calif.). The reverse transcribed samples were amplified by PCR technique using Taq polymerase core kit (Qiagen, Valencia, Calif.). RT-PCR was used to detect the p35 subunit as well as β-actin promoter and pCAGGS. The primers synthesized from 5' to 3' were as follows: For pmIL-12 (p35), 5'-GTC TCC CAA GGT CAG CGT TCC-3' upstream and 5'-CTG GTT TGG TCC CGT GTG ATG-3' downstream. For β-actin, 5'-ATG GTG GGA ATG GGT CAG AAG-3' upstream and 5'-CAC GCA GCT CAT TGT AGA AGG-3' downstream. For pCAGGS, 5'-GCC AAT AGG GAC TTT CCA T-3' upstream and 5'-GGT CAT GTA CTG GGC ATA ATG-3' downstream primer, respectively. The PCR cycling conditions were as follows: Denaturing at 95° C. for 15 secs, annealing at 56° C. for 15 secs, and extension at 72° C. for 30 secs. A total of 35 cycles were run for product amplification. The PCR product was separated by electrophoresis using 1% agarose gel. The expected size of the PCR product from mIL-12 p35 mRNA was 297 bp and 150 bp for β-actin.

Figure 8:
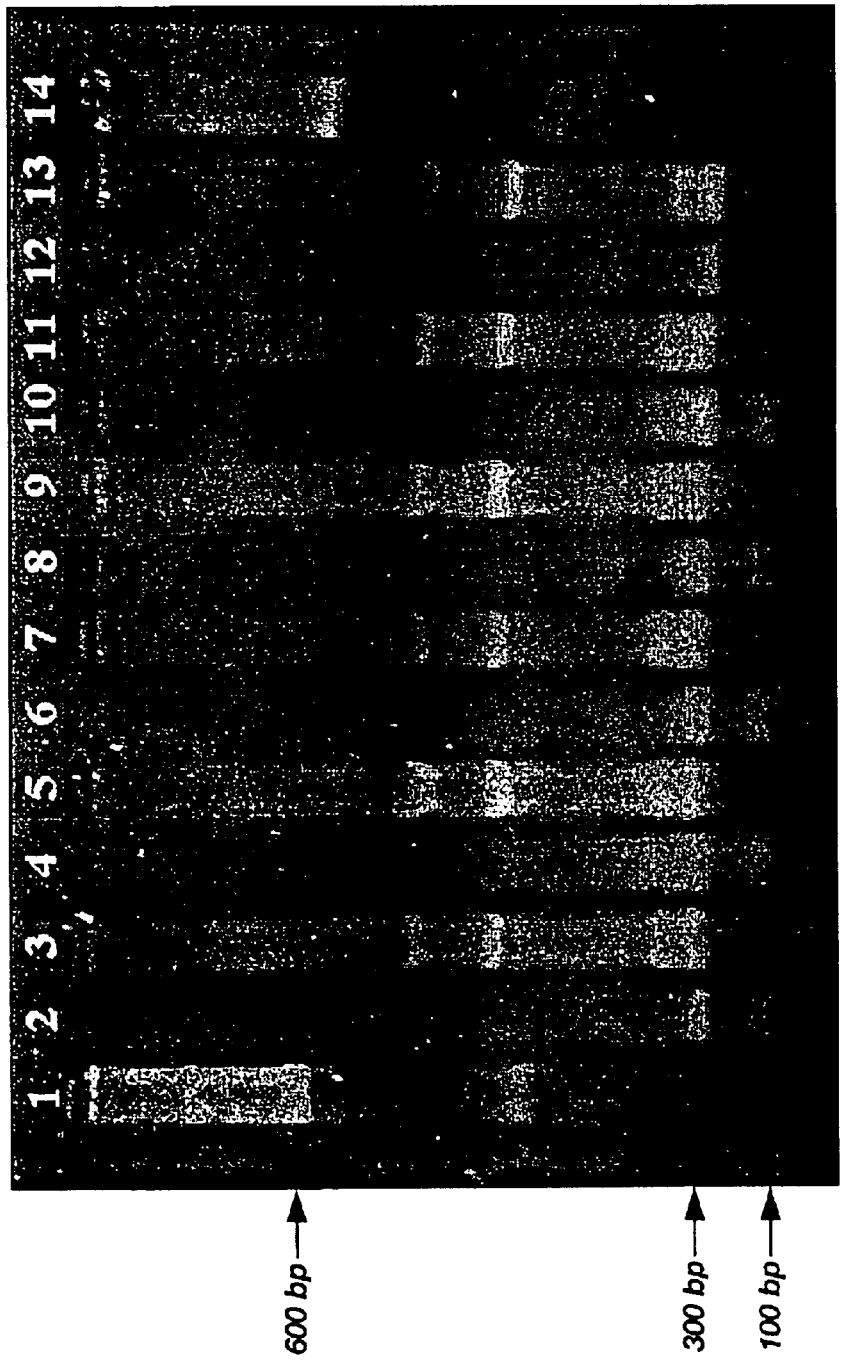
FIG. 8 illustrates RT-PCR assay of CT-26 colon adenocarcinoma cells after being transfected in vitro by PEACE:DOPE liposome/pmIL-12 complexes.

As illustrated in FIG. 8, RT-PCR results show that the mIL-12 p35 production at mRNA level is sufficient enough to induce the formation of mIL-12 p70 by forming disulphide linkages with mIL-12 p40. The β-actin control confirmed that mIL-12 gene expression was indeed from the plasmid encoding mIL-12 and not from endogenous production of mIL-12 by the cells. The bands obtained from RT-PCR suggest that the mIL-12 expression at protein levels should be considerably high and mIL-12 p70 secreted from the transfected CT-26 cells should also be very high if the relative production of mIL-12 p35 and IL-12 p40 are close to each other.

EXAMPLE 13

In Vivo Gene Expression

Depending on the particle size and surface charge of water soluble PEACE/pDNA and water insoluble PEACE:DOPE liposomes/pDNA complexes can be delivered to most of the major organs, such as lung, liver, spleen and distal tumors after systemic administration. For effective gene delivery to the hepatocytes, these complexes must be stable in blood and their particle size should be below 100 nm for extravasation through the sinusoidal hepatic endothelium and access the Space of Disse. These particles should also have specific ligands such as galactose or lacatose to promote binding to the hepatocyte receptors, and internalization through receptor-mediated endocytosis. It was possible to produce 60~150 nm size water soluble PEACE/pDNA and PEACE:DOPE liposome/pDNA complexes for in vivo applications.

This example illustrates in vivo gene expression using a PEACE:DOPE cationic liposome of the present invention as a gene carrier. It describes the transfer and expression of plasmid pmIL-12 into the lung of mice after systemic administration at a dose of 0.25 mg DNA/mouse using 150 µL as the injection volume. It demonstrates the especially advantageous properties of the cationic liposome compositions according to the present invention, in particular for gene therapy applications.

CT-26 colon adeno-carcinoma cells were injected intravenously into BALB/c mice to generate pulmonary metastases to assess the in vivo gene transfer efficiency of PEACE:DOPE liposomes/pmIL-12 complexes injected intravenously. At 48 hrs after intravenous injection of PEACE:DOPE liposomes/pmIL-12 complexes, the lungs were harvested, chopped into small pieces, re-cultured for 24 hours and the culture supernatants were analyzed by ELISA. The mIL-12 production was high in the lung. One of the most important properties of mIL-12 is its ability to induce production of large amounts of mIFN-γ. Therefore, we also measured the levels of mIFN-γ induced by mIL-12. PEACE:DOPE liposomes/pmIL-12 complexes produced much higher levels of mIFN-γ compared to naked pmIL-12 or PEACE:DOPE liposomes.

Due to the small size of water soluble PEACE/pDNA complexes, we expect these complexes to be especially useful for intra-tumoral gene delivery as well as for systemic delivery to the hepatocytes and distal tumors. To minimize the plasma protein binding, small size poly(ethyelene glycol) (PEG) can be attached to the PEI head-group of water soluble PEACE.

Thus, among the various embodiments taught there has been disclosed a composition comprising a novel cationic lipopolymer and method of use thereof for delivering bioactive agents, such as DNA, RNA, oligonucleotides, proteins, peptides, and drugs, by facilitating their transmembrane transport or by enhancing their adhesion to biological surfaces. It will be readily apparent to those skilled in the art that various changes and modifications of an obvious nature may be made without departing from the spirit of the invention, and all such changes and modifications are considered to fall within the scope of the invention as defined by the appended claims.

We claim:

1. The cationic lipopolymer poly{(ethylene imine)-co-[N-2-aminoethyl ethylene imine]-co-[N-(N-cholesteryloxycarbonyl-(2-aminoethyl))ethylene imine]} ("PEACE").

2. A biodegradable cationic lipopolymer comprising a branched polyethylenimine (PEI) a $C_{12}$ to $C_{18}$ fatty acid, and a biodegradable linker, wherein the biodegradable linker covalently links the branched PEI and the $C_{12}$ to $C_{18}$ fatty acid and wherein the cationic lipopolymer further comprises a targeting moiety selected from the group consisting of transferrin, asialoglycoprotein, antiobodies, antibody fragments, low density lipoproteins, interleukins, GM-CSF, G-CSF, M-CSF, stem cell factors, erythropoietin, epidermal growth factor (EGF), insulin, asialoorosomucoid, mannose-6-phosphate, mannose, Lewis$^x$ and sialyl Lewis$^x$, N-acetyllactosamine, galactose, lactose, thrombomodulin, fusogenic agents, polymixin B, hemagglutinin HA2, lysomotrophic agents, and nucleus localization signals (NLS).

3. The cationic lipopolymer of claim 1, wherein at least one primary amine of the cationic lipopolymer (PEACE) is grafted with a polyalkylene glycol, and the cationic lipopolymer (PEACE) contains at least 50% unsubstituted free amino functional groups.

4. The cationic lipopolymer of claim 3, wherein the polyalkylene glycol is polyehtylene glycol (PEG).

5. The cationic lipopolymer of claim 4, wherein the polyethylene glycol has a molecular weight of between 500–20,000 Daltons.

6. The cationic lipopolymer of claim 5 wherein said PEG has molecular weight of between 500–20,000 Daltons.

7. The cationic lipopolymer of claim 3, further comprising a targeting moiety selected from the group consisting of transferrin, asialoglycoprotein, antibodies, antibody fragments, low density lipoproteins, interleukins, GM-CSF, G-CSF, M-CSF, stem cell factors, erythropoietin, epidermal growth factor (EGF), insulin, asialoorosomucoid, mannose-6-phosphate, mannose, Lewis$^x$ and sialyl Lewis$^x$, N-acetyllactosamine, galactose, lactose, thrombomodulin, fusogenic agents, polymixin B, hemaglutinin HA2, lysosomotrophic agents and nucleus localization signals (NLS).

8. The cationic lioopolymer of claim 7 wherein said targeting moiety is a fusogenic agent selected from the group consisting of polymixin B and hemagglutinin HA2.

9. The cationic lipopolymer of claim 7 wherein said targeting moiety is a nucleus localizing signal which is a T-antigen.

10. The cationic lipopolymer of claim 7 wherein the targeting moiety is galactose.

11. The cationic lipopolymer of claim 7 wherein the targeting moiety is lactose.

12. The cationic lipopolymer of claim 3 wherein the targeting moiety is bonded to a free amine group of the branched PEI or to polyethylene glycol.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<221> NAME/KEY: primer_bind
<223> OTHER INFORMATION: PCR primer

<400> SEQUENCE: 1
gtctcccaag gtcagcgttc c                                              21

<210> SEQ ID NO 2
<211> LENGTH: 21
<212> TYPE: DNA
<213> ORGANISM: Artificial Sequence
<220> FEATURE:
<221> NAME/KEY: primer_bind
<223> OTHER INFORMATION: PCR primer

<400> SEQUENCE: 2
ctggtttggt cccgtgtgat g                                              21

<210> SEQ ID NO 3
<211> LENGTH: 21
<212> TYPE: DNA
<213> ORGANISM: Artificial Sequence
<220> FEATURE:
<221> NAME/KEY: primer_bind
<223> OTHER INFORMATION: PCR primer

<400> SEQUENCE: 3
atggtgggaa tgggtcagaa g                                              21

<210> SEQ ID NO 4
<211> LENGTH: 21
<212> TYPE: DNA
<213> ORGANISM: Artificial Sequence
<220> FEATURE:
<221> NAME/KEY: primer_bind
<223> OTHER INFORMATION: PCR primer

<400> SEQUENCE: 4
cacgcagctc attgtagaag g                                              21
```

```
<210> SEQ ID NO 5
<211> LENGTH: 19
<212> TYPE: DNA
<213> ORGANISM: Artificial Sequence
<220> FEATURE:
<221> NAME/KEY: primer_bind
<223> OTHER INFORMATION: PCR primer

<400> SEQUENCE: 5
gccaataggg actttccat                                              19

<210> SEQ ID NO 6
<211> LENGTH: 21
<212> TYPE: DNA
<213> ORGANISM: Artificial Sequence
<220> FEATURE:
<221> NAME/KEY: primer_bind
<223> OTHER INFORMATION: PCR primer

<400> SEQUENCE: 6
ggtcatgtac tgggcataat g                                           21
```